(12) United States Patent  
Kwong et al.

(10) Patent No.: US 9,139,494 B2  
(45) Date of Patent: Sep. 22, 2015

(54) TRIPHENYLENE HOSTS IN PHOSPHORESCENT LIGHT EMITTING DIODES

(75) Inventors: Raymond Kwong, Plainsboro, NJ (US); Bert Alleyne, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 741 days.

(21) Appl. No.: 13/233,213

(22) Filed: Sep. 15, 2011

(65) Prior Publication Data

US 2012/0032156 A1  Feb. 9, 2012

Related U.S. Application Data

(63) Continuation of application No. 11/443,586, filed on May 31, 2006.

(60) Provisional application No. 60/686,094, filed on May 31, 2005.

(51) Int. Cl.

| | | |
|---|---|---|
| H01L 51/50 | (2006.01) | |
| C07C 13/62 | (2006.01) | |
| C07C 15/38 | (2006.01) | |
| C09K 11/06 | (2006.01) | |
| C09K 19/32 | (2006.01) | |
| H01L 51/00 | (2006.01) | |
| H05B 33/14 | (2006.01) | |

(52) U.S. Cl.
CPC ............. *C07C 13/62* (2013.01); *C07C 15/38* (2013.01); *C09K 11/06* (2013.01); *C09K 19/32* (2013.01); *H01L 51/0008* (2013.01); *H01L 51/0054* (2013.01); *H01L 51/0056* (2013.01); *H01L 51/0057* (2013.01); *H01L 51/0058* (2013.01); *H05B 33/14* (2013.01); *C07C 2103/42* (2013.01); *C07C 2103/54* (2013.01); *C09K 2019/328* (2013.01); *C09K 2211/1007* (2013.01); *C09K 2211/1011* (2013.01); *C09K 2211/1416* (2013.01); *H01L 51/5016* (2013.01); *Y10S 428/917* (2013.01)

(58) Field of Classification Search
USPC ................. 428/690, 917; 313/504, 505, 506; 257/40, 51.026, E51.052
See application file for complete search history.

(56) References Cited

U.S. PATENT DOCUMENTS

| | | |
|---|---|---|
| 3,711,567 A | 1/1973 | Innes |
| 5,281,489 A | 1/1994 | Mori et al. |
| 5,621,131 A | 4/1997 | Kreuder et al. |
| 5,858,563 A | 1/1999 | Sano et al. |
| 5,972,247 A | 10/1999 | Shi et al. |
| 5,989,737 A | 11/1999 | Xie et al. |
| 6,099,750 A | 8/2000 | Simmerer et al. |
| 6,150,042 A | 11/2000 | Tamano et al. |
| 6,245,449 B1 | 6/2001 | Tamano et al. |
| 6,361,886 B2 | 3/2002 | Shi et al. |
| 6,492,041 B2 | 12/2002 | Ishikawa et al. |
| 6,582,837 B1 | 6/2003 | Toguchi et al. |
| 6,635,364 B1 | 10/2003 | Igarashi et al. |
| 6,733,849 B2 | 5/2004 | Inoue et al. |
| 6,830,829 B2 | 12/2004 | Suzuki et al. |
| 6,861,163 B2 | 3/2005 | Cheng et al. |
| 6,897,913 B2 | 5/2005 | Tsuboyama et al. |
| 7,183,010 B2 | 2/2007 | Jarikov |
| 2004/0005404 A1 | 1/2004 | Suzuri et al. |
| 2004/0076853 A1 | 4/2004 | Jarikov |
| 2004/0131881 A1 | 7/2004 | Zheng et al. |
| 2005/0025993 A1 | 2/2005 | Thompson et al. |
| 2005/0112407 A1 | 5/2005 | Ogasawara et al. |
| 2006/0134456 A1 | 6/2006 | Ikeda et al. |
| 2006/0231843 A1 | 10/2006 | Qin et al. |
| 2009/0045731 A1 | 2/2009 | Nishimura et al. |

FOREIGN PATENT DOCUMENTS

| | | |
|---|---|---|
| JP | 11-283748 | 10/1999 |
| JP | 2002 063988 | 2/2002 |
| JP | 2005-71983 | 3/2005 |
| JP | 2005 071983 | 3/2005 |
| JP | 2005-259472 | 9/2005 |
| JP | 2005 259472 | 9/2005 |

OTHER PUBLICATIONS

Mueller et al., 1996, "Polybenzoid C54 Hydrocarbons: Synthesis Structural Characterization in Vapor-deposited ordered monolayers", Angewandte Chemie International Edition, 35(8): 886-888.
European Search Report for European Patent Application No. 10 009 894.6 mailed on Apr. 1, 2011.
Bacher et al., "Triphylenes: A new class of hole transport material in organic light emitting diodes", SPIE, Dec. 1, 1997, pp. 313-320, vol. 3148, SPIE US.
Kumar et al., Recent Developments . . . triphenylene . . . , 2004, Liquid Crystals, vol. 31, pp. 1037-1059.
Wegewijs et al., Charge mobilites . . . triphenylene derivatives, 2002, Physical Reviews B, vol. 25, pp. 245112-1 to 245112-8.
Notice of Reasons for Rejection issued on Oct. 1, 2013 for corresponding Japanese Application No. 2012-7774 .
Office Action issued on Jul. 16, 2014 for corresponding Chinese Application No. 201310386045.2.
Office Action issued on Aug. 30, 2014 for corresponding Korean Application No. 10-2014-7013012.

*Primary Examiner* — Gregory Clark
(74) *Attorney, Agent, or Firm* — Duane Morris LLP

(57) ABSTRACT

An organic emissive layer is provided. Also provided is a device in which the organic emissive layer is disposed between an anode and a cathode. The organic emissive layer includes a phosphorescent material and triphenylene compound or a compound having a repeat unit having a triphenylene moiety. The triphenylene is optionally substituted. The substituents may be the same or different and each is selected from the group consisting of alkyl, aryl, fused aryl, substituted aryl, alkenyl, alkynyl, and heteroalkyl. Triphenylene compounds are also provided.

19 Claims, 25 Drawing Sheets

2,2-BT:Ir(pq)$_2$(acac)

Device structures

|  | CuPc | NPD | EML | Dopant % | BL | Alq |
|---|---|---|---|---|---|---|
| Example 16 | 100 | 500 | 300 | 6 | BAlq 150 | 500 |
| Example 17 | 100 | 350 | 300 | 6 | HPT 50 | 600 |
| Example 18 | 100 | 500 | 300 | 6 |  | 500 |
| Comparative Example 4 | 100 | 500 | 300 | 6 | BAlq 150 | 500 |
| Comparative Example 5 | 100 | 350 | 300 | 4.5 | HPT 50 | 600 |

FIG. 18

H1NT:Ir(pq)$_2$(acac)

H2BT:Ir(3-Meppy)$_3$

Device structures

|  | CuPc | NPD | EML | Host | Dopant % | BL | Alq$_3$ |
|---|---|---|---|---|---|---|---|
| Example 22 | 100 | 350 | 300 | H1NT | Ir(pq)$_2$(acac) 6% | BAlq 150 | 450 |
| Example 23 | 100 | 300 | 300 | H2BT | Ir(3-Meppy)$_3$ 10% | HPT 50 | 450 |

FIG. 27

TRIPHENYLENE HOSTS IN PHOSPHORESCENT LIGHT EMITTING DIODES

REFERENCE TO RELATED APPLICATION

This application is a continuation of U.S. application Ser. No. 11/443,586, filed May 31, 2006, which is related to and claims priority to U.S. Provisional Application Ser. No. 60/686,094 filed May 31, 2005, all of which are incorporated herein by reference in their entireties.

FIELD OF THE INVENTION

The present invention relates to organic light emitting devices (OLEDs), and specifically to phosphorescent organic materials used in such devices. More specifically, the present invention relates to triphenylene compounds incorporated into OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY OF THE INVENTION

The present invention is directed to triphenylene compounds useful in phosphorescent organic light emitting diodes. Specific examples include multi-aryl-substituted triphenylenes such as hexaryltriphenylenes, 1,1-bistriphenylenes, 2,2-bistriphenylenes, 1,12-fused-bistriphenylenes, 2,3-fused-tetratriphenylenes, and arylenetriphenylene triphenylenes. The advantages are the high triplet energy, yet high π-conjugation. High efficiency and stability PHOLEDs with triphenylene hosts are demonstrated. Some high triplet energy analogs are expected to work with deep blue phosphorescent dopants.

An emissive layer in an organic light emitting device is provided. The emissive layer includes a phosphorescent material and a triphenylene compound. Preferably the triphenylene compound has an energy gap between the HOMO and the LUMO energy levels that is larger than the energy gap between the HOMO and the LUMO energy levels of the phosphorescent material.

In a preferred embodiment, the triphenylene compound in the emissive layer has an energy gap between its HOMO energy level and its LUMO energy level of at least about 1.8 eV.

In another embodiment, the triphenylene compound has a highest occupied molecular orbital that is lower than the highest occupied molecular orbital of the phosphorescent material.

In another embodiment, the triphenylene compound has a lowest unoccupied molecular orbital that is higher than the lowest unoccupied molecular orbital of the phosphorescent material.

In one embodiment, the emissive layer comprises a phosphorescent material and a triphenylene compound wherein the triphenylene compound has the formula

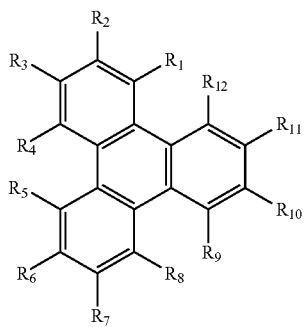

Where each $R_1, R_2, R_3, R_4, R_5, R_6, R_7, R_8, R_9, R_{10}, R_{11}$ and $R_{12}$ is independently H or a substituent selected from the group consisting of aryl, substituted aryl, heteroaryl, substituted heteroaryl, alkyl, arylkyl heteroalkyl, alkenyl, and alkynyl and wherein the triphenylene compound has at least two substituents. Preferably, the triphenylene compound has a molecular weight of less than 1400. In some preferred embodiments, at least one of $R_1$, $R_2$, $R_3$, $R_4$, $R_5$, $R_6$, $R_7$, $R_8$, $R_9$, $R_{10}$, $R_{11}$ and $R_{12}$ is selected from aryl and substituted aryl. In another embodiment, each of $R_2$, $R_3$, $R_6$, $R_7$, $R_{10}$, and $R_{11}$ is selected from aryl and substituted aryl and in yet another embodiment, each of $R_2$, $R_3$, $R_6$, $R_7$, $R_{10}$, and $R_{11}$ is selected from aryl and substituted aryl and $R_2$, $R_3$, $R_6$, $R_7$, $R_{10}$, and $R_{11}$ are all the same.

In another embodiment, the emissive layer comprises a phosphorescent material and a compound having a repeat unit, the repeat unit containing a triphenylene moiety.

In another embodiment, the emissive layer comprises a phosphorescent material and a triphenylene compound having a benzotriphenylene structure.

In another embodiment, the emissive layer comprises a phosphorescent material and a triphenylene compound having a fused-triphenylene structure.

An organic electroluminescent device is also provided. The device comprises an anode, a cathode, and an emissive layer comprising a triphenylene material and a phosphorescent material between the anode and the cathode. The triphenylene material may be a fused triphenylene, a benzotriphenylene, or a triphenylene compound having the formula

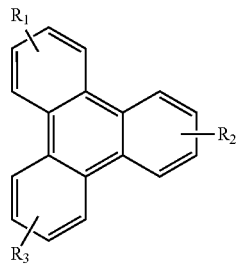

where $R_1$-$R_3$ are each independently H or a substituent selected from the group consisting of, aryl, substituted aryl, heteroaryl, substituted heteroaryl, alkyl, arylkyl, heteroalkyl, alkenyl, and alkynyl. Preferably the triphenylene compound has at least two substituents and a molecular weight of less than 1400.

Also provided is an organic electroluminescent device comprising an anode, a cathode, and an emissive layer between the anode and the cathode, the emissive layer comprising a phosphorescent material and a compound having a repeat unit, the repeat unit containing a triphenylene moiety.

BRIEF DESCRIPTION OF THE DRAWINGS

FIG. 18 shows the 2,2-BT:Ir(pq)$_2$(acac) device compositions.

FIG. 27 shows the H1NT:Ir(pq)$_2$(acac) and H2BT:Ir(3-Meppy)$_3$ device composition

DETAILED DESCRIPTION

Figure 1:
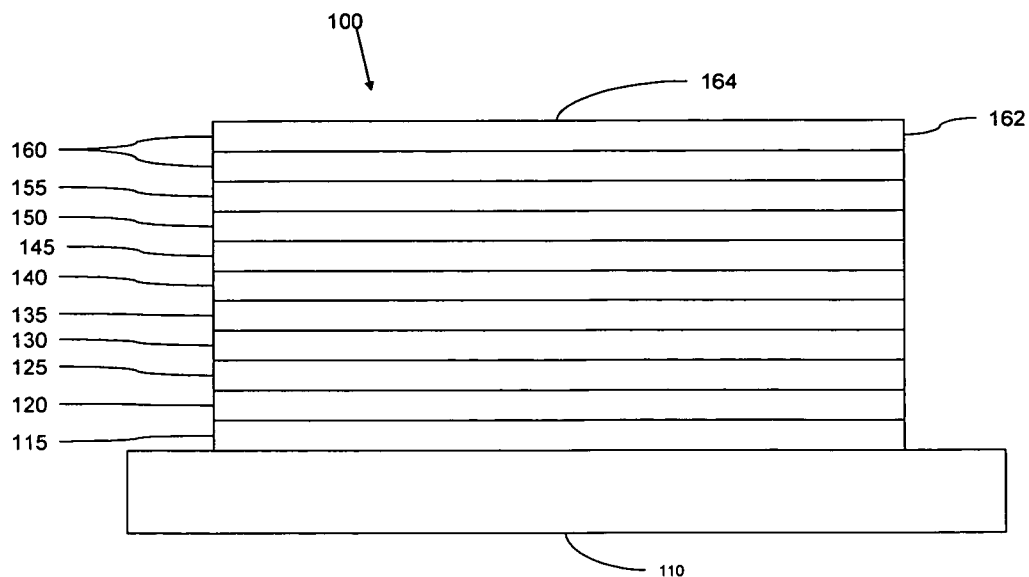
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organo-metallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice, organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials in OLEDs include $Alq_3$, CBP and mCP. Examples of emissive and host materials in OLEDs are disclosed in U.S. Pat. No. 6,303,238 to Thompson et al., which is incorporated by reference in its entirety. In the present invention, preferred host materials include triphenylene complexes. Triphenylene compounds are useful materials in other applications in OLEDs such as electron transporting materials as described in US US20050025993. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the luminescent properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels directly involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that Cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2, and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one of skill in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the in and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
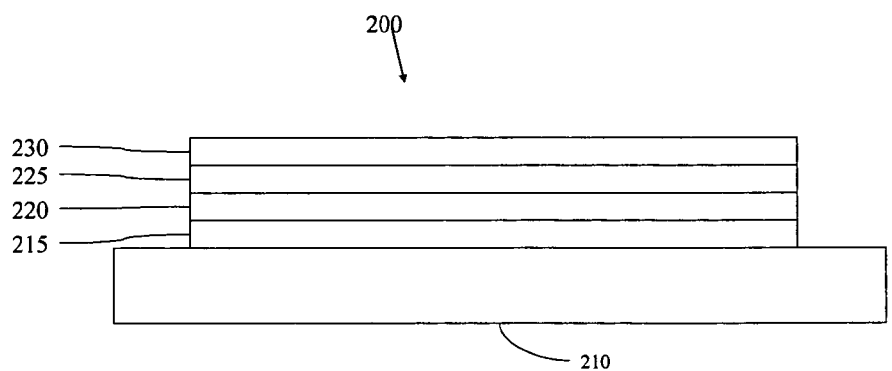
FIG. 2 shows an inverted organic light emitting device that does not have a separate electron transport layer.
Figure 4:
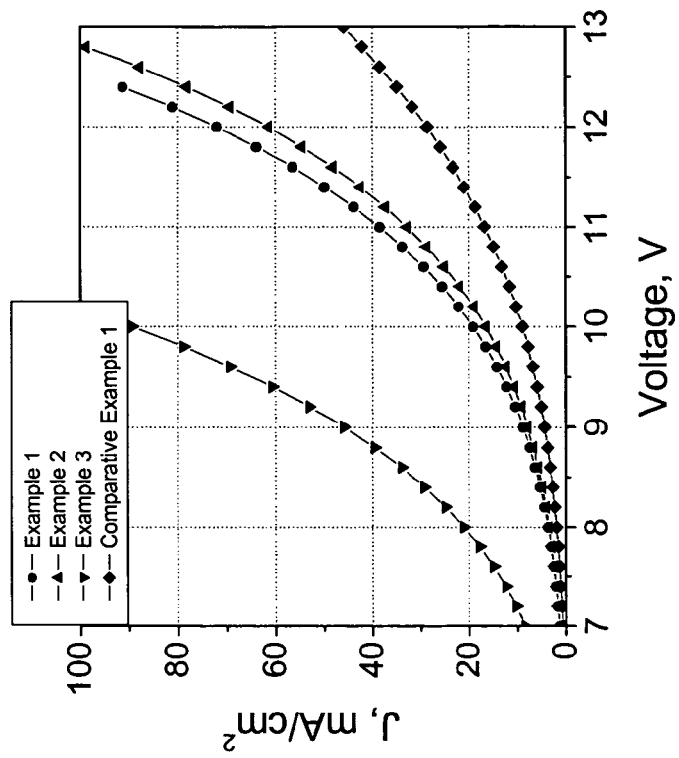
FIG. 4 shows current density vs voltage of HPT:Ir(3-Mepq)$_2$(acac) devices.
Figure 3:
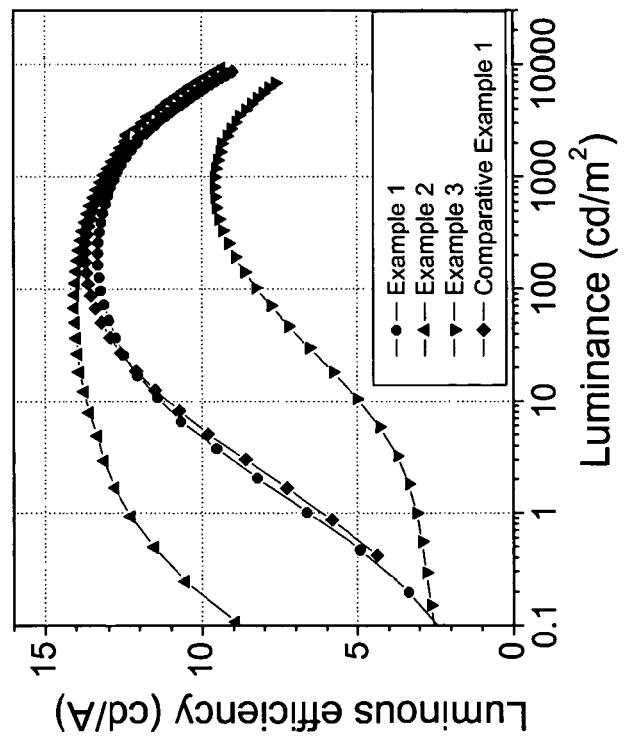
FIG. 3 shows luminous efficiency vs luminance of HPT:Ir (3-Mepq)$_2$(acac) devices.
Figure 5:
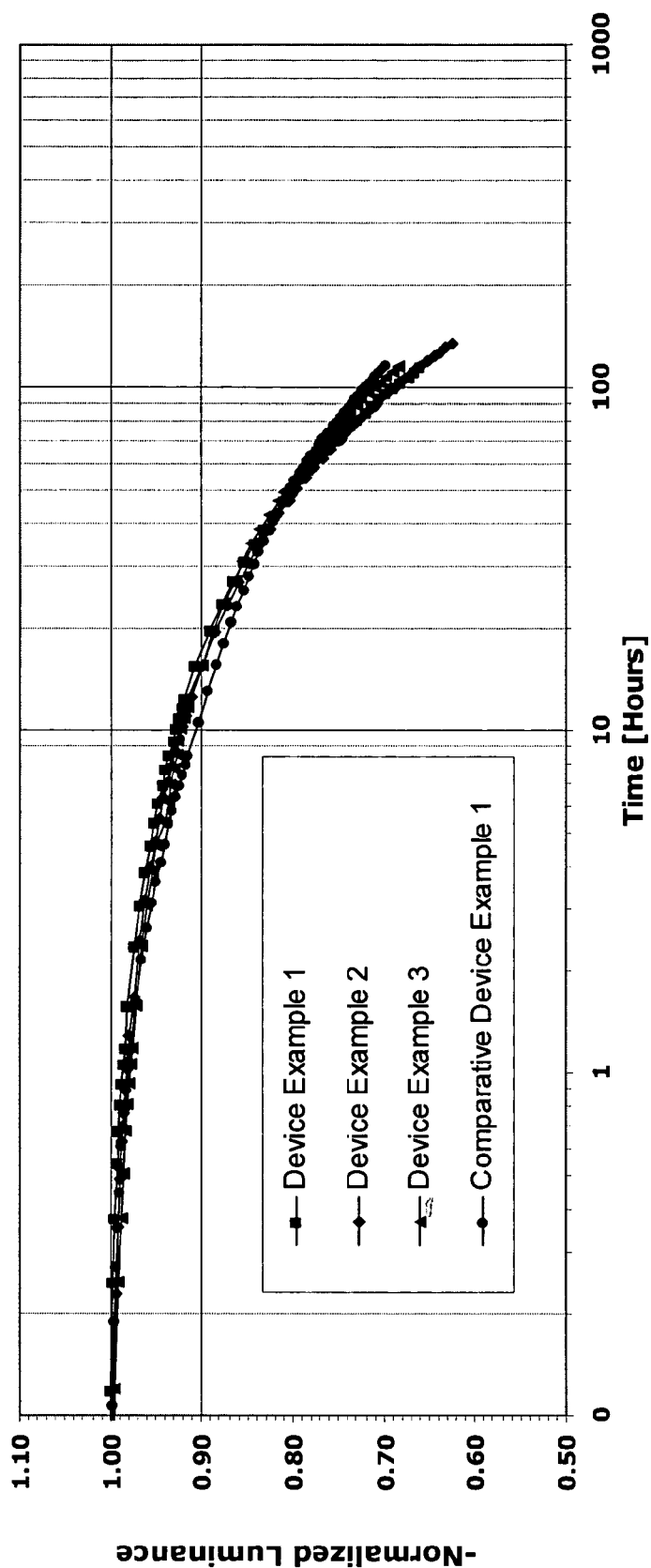
FIG. 5) shows lifetime of HPT:Ir(3-Mepq)$_2$(acac) devices
Figure 7:
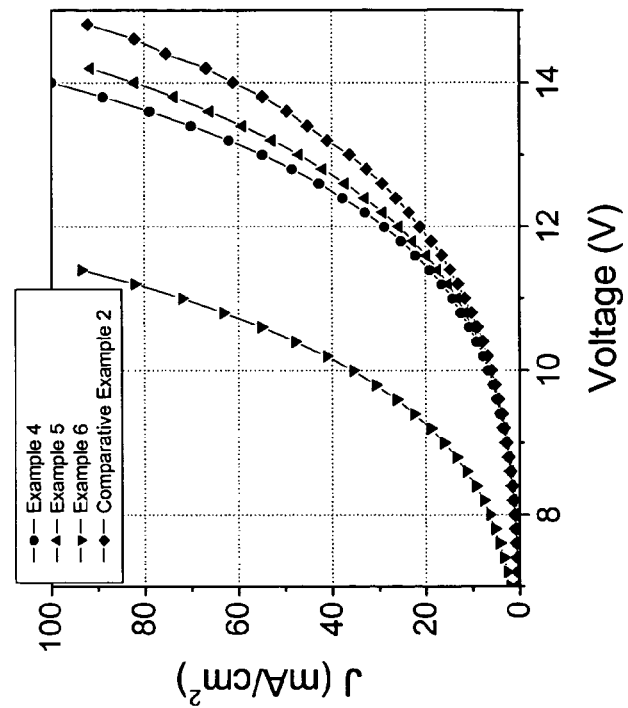
FIG. 7 shows current density vs voltage of HPT:Ir(1-piq)$_3$ devices.
Figure 6:
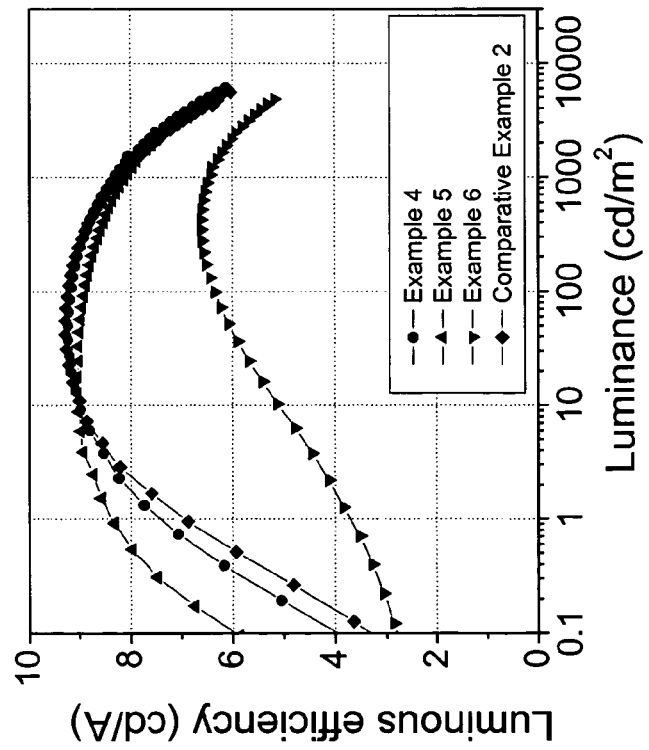
FIG. 6 shows luminous efficiency vs luminance of HPT:Ir (1-piq)$_3$.
Figure 8:
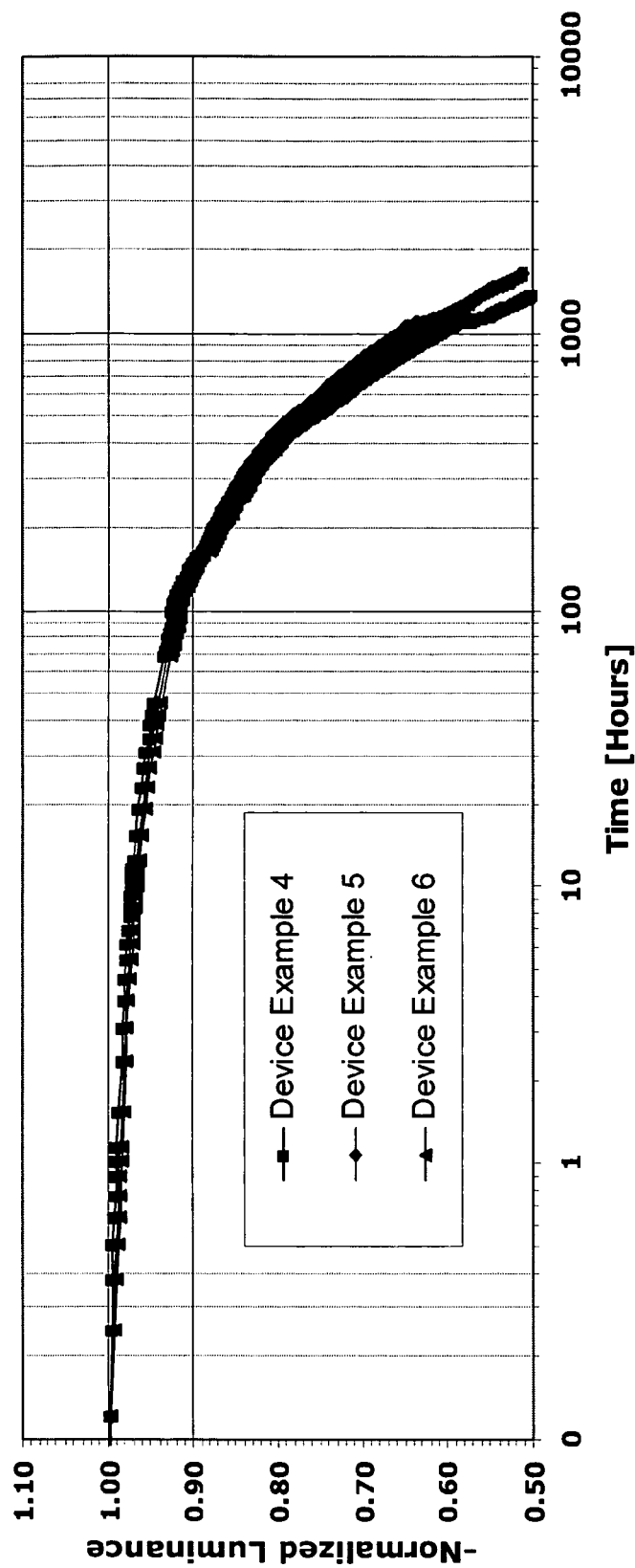
FIG. 8 shows lifetime of HPT:Ir(1-piq)$_3$ devices.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, $C(O)R$, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two atoms are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to four heteroatoms, for example, pyrrole, furan, thiophene, imidazole, oxazole, thiazole, triazole, tetrazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

The present invention is directed to an organic emissive layer comprising a phosphorescent material and a triphenylene compound, as well as a device including such an emissive layer. Specific triphenylene compounds are also provided. In preferred embodiments of the invention, the organic emissive layer includes a phosphorescent material and a triphenylene compound, optionally substituted. The substituents may be the same or different and each is selected from the group consisting of alkyl, aryl, substituted aryl, alkenyl, alkynyl, and heteroalkyl. Particularly preferred are triphenylene compounds having a molecular weight of less than 1400 that can be evaporated at vacuum without decomposition. High efficiency and lifetime are demonstrated by devices fabricated according to the present invention. The high triplet energy of triphenylene renders triphenylene compounds particularly suitable as hosts or co-hosts for use with deep blue phosphorescent dopants.

Triphenylene is a polyaromatic hydrocarbon with a high triplet energy and a relatively small energy difference between the first singlet and first triplet levels. This would indicated that triphenylene has relatively easily accessible HOMO and LUMO levels compared to other aromatic compounds with similar triplet energy (e.g., biphenyl). The advantage of using triphenylene and its derivatives as hosts is that it can accommodate red, green and even blue phosphorescent dopants to give high efficiency without energy quenching.

Preferably the triphenylene compound in the present invention has an energy gap between the HOMO and the LUMO energy levels that is larger than the energy gap between the HOMO and the LUMO energy levels of the phosphorescent material.

In a preferred embodiment, the triphenylene compound in the present invention has an energy gap between its HOMO energy level and its LUMO energy level of at least about 1.8 eV.

In another embodiment, the triphenylene compound has a highest occupied molecular orbital that is lower than the highest occupied molecular orbital of the phosphorescent material.

In another embodiment, the triphenylene compound has a lowest unoccupied molecular orbital that is higher than the lowest unoccupied molecular orbital of the phosphorescent material.

In one embodiment, the present invention provides an organic emissive layer comprising a phosphorescent material and a triphenylene compound, as well as a device including said emissive layer, wherein the triphenylene compound comprises a multi-aryl-substituted triphenylene, preferably 2,3,6,7,10,11-hexaaryltriphenylene having the structure:

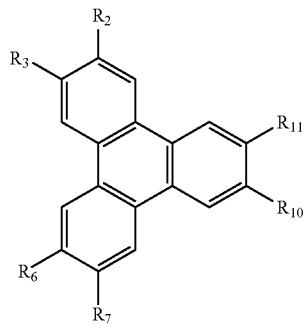

wherein $R_2$, $R_3$, $R_6$, $R_7$, $R_{10}$ and $R_{11}$ is each independently H or a substituent selected from the group consisting of aryl, substituted aryl, heteroaryl, substituted heteroaryl, alkyl, arylkyl, heteroalkyl, alkenyl, and alkynyl; and wherein the triphenylene compound has at least two substituents.

$R_2$, $R_3$, $R_6$, $R_7$, $R_{10}$ and $R_{11}$ may all be the same or they may be different. In one embodiment, each of $R_2$, $R_3$, $R_6$, $R_7$, $R_{10}$ and $R_{11}$ is selected from aryl and substituted aryl Preferably, at least one of $R_2$, $R_3$, $R_6$, $R_7$, $R_{10}$ and $R_{11}$ is selected from aryl and substituted aryl. Preferred are phenyl, naphthyl and biphenyl, optionally substituted.

Preferred multi-aryl-substituted triphenylene compounds are those that can be evaporated at vacuum without decomposition. Examples include but are not limited to compounds where $R_2$, $R_3$, $R_6$, $R_7$, $R_{10}$ and $R_{11}$ are phenyl, naphthyl and biphenyl as shown by the following structures:

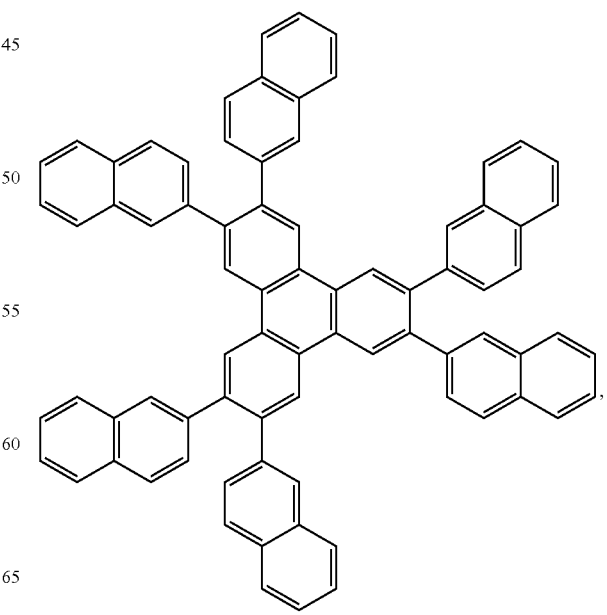

-continued
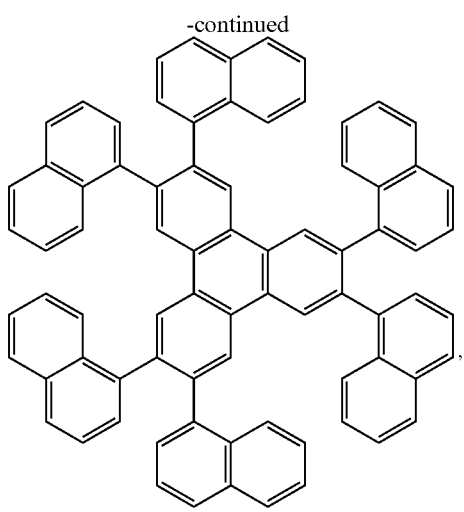
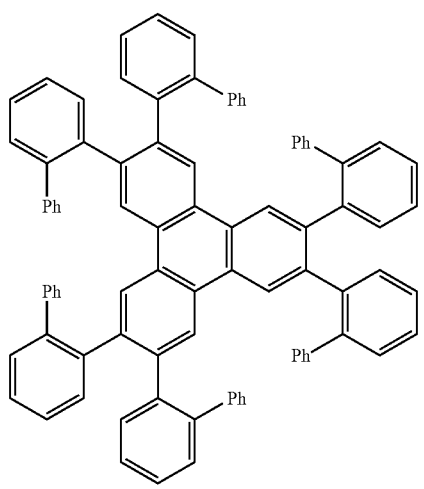
-continued
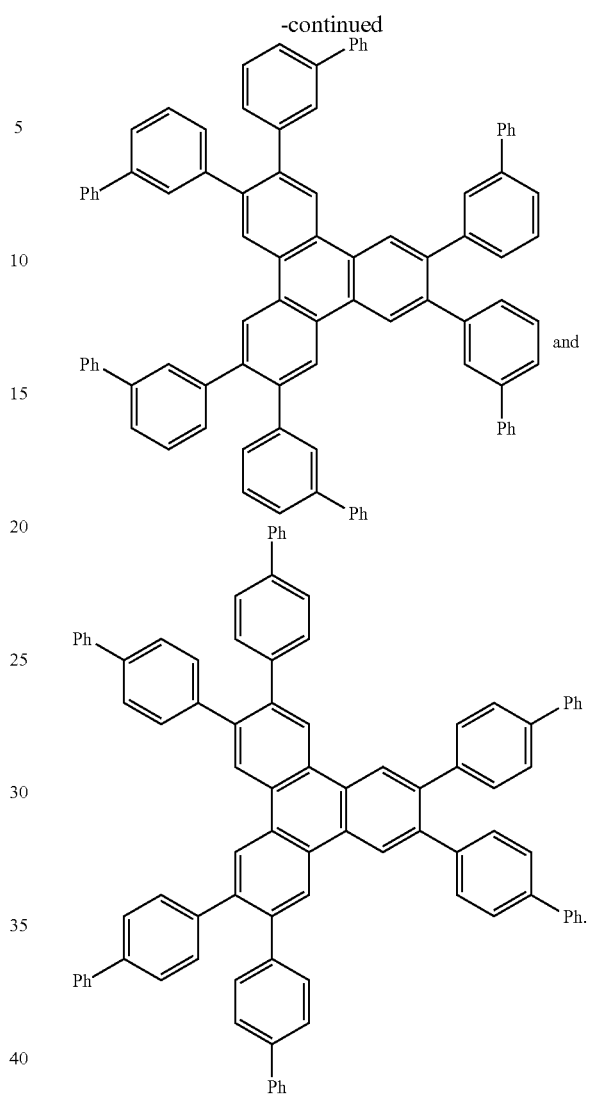
In another example, $R_2$, $R_3$, $R_6$, $R_7$, $R_{10}$ and $R_{11}$ are all substituted phenyl. Such an example includes but is not limited to a compound having the structure
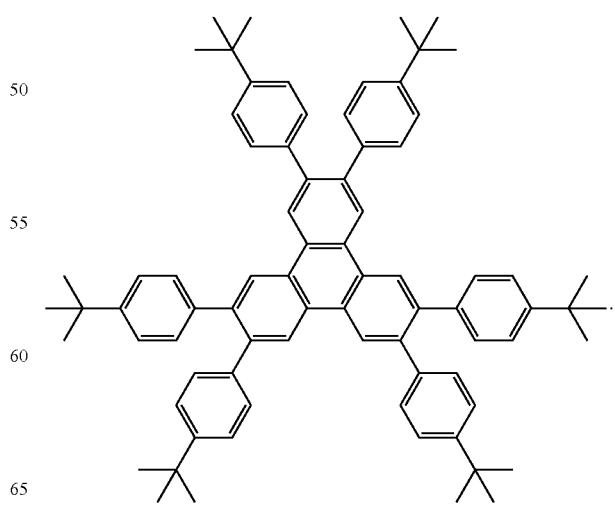

In another embodiment, the present invention provides an organic emissive layer comprising a phosphorescent material and a compound having a repeating unit containing a triphenylene moiety, as well as a device including said emissive layer.

Compounds having a repeating unit containing a triphenylene moiety include arylenetriphenylene having the structure

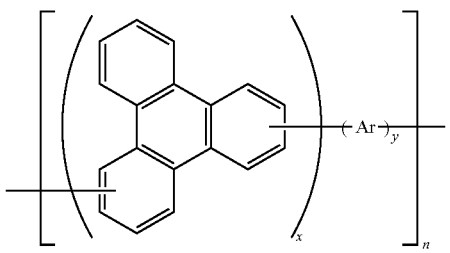

Where
Ar is selected from aryl and substituted aryl
X is 1-3;
Y is 1-3 and
n is 1-3

A preferred arylenetriphenylene is phenylenetriphenylene having the structure

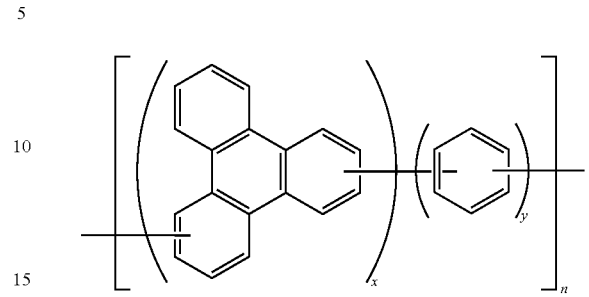

Where
X is 1-3;
Y is 1-3 and
n is 1-3.

More preferred arylenetriphenylene compounds are those that can be evaporated at vacuum without decomposition. Examples include but are not limited to:

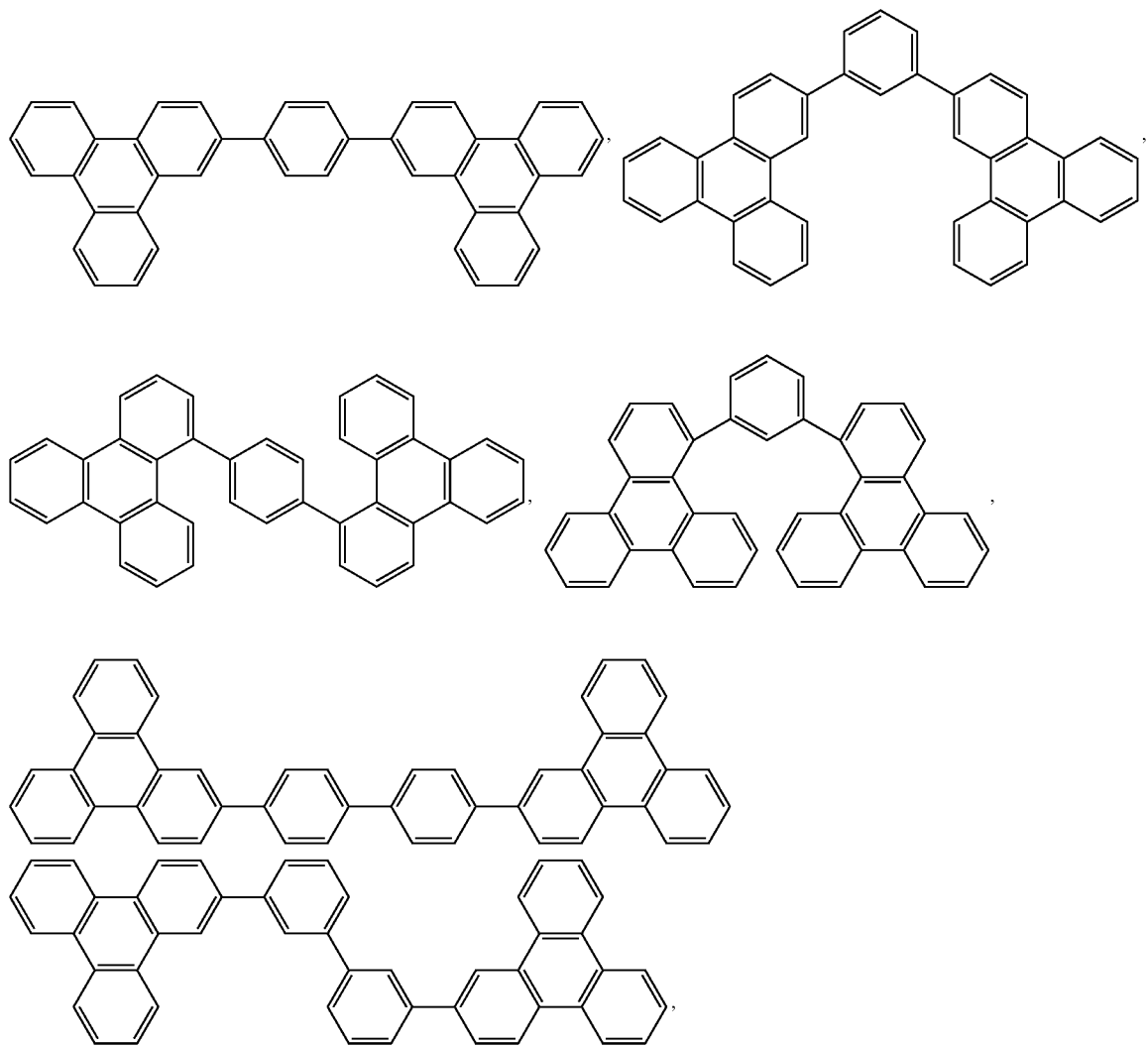

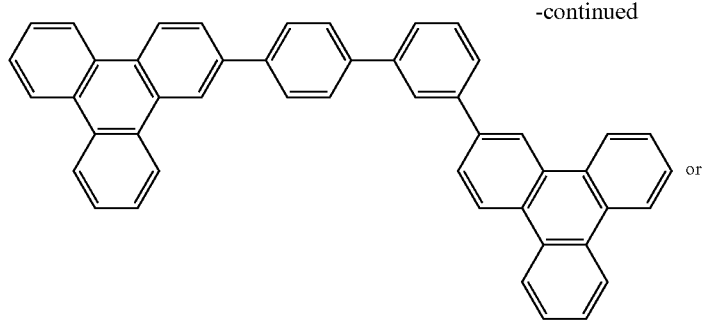

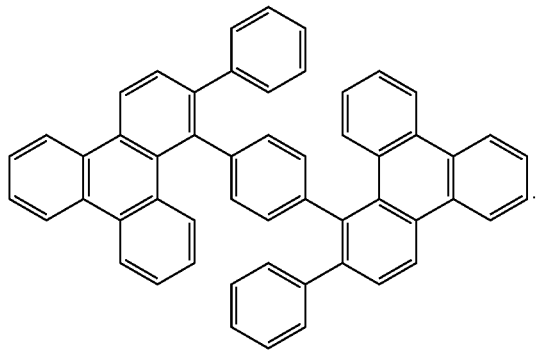 [SMILES: c1ccc(-c2ccc3c4ccccc4c4ccccc4c3c2-c2ccc(-c3c(-c4ccccc4)ccc4c5ccccc5c5ccccc5c34)cc2)cc1]

Compounds having a repeating unit containing a triphenylene moiety also include triphenylenylene having the structure

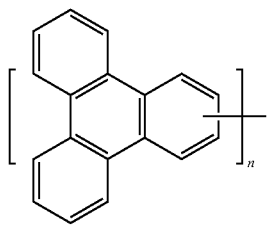

Preferred triphenylenylene compounds are oligo(triphenylenylene) where n≤5. More preferred are triphenylenylene compounds that can be evaporated at vacuum without decomposition. Examples include but are not limited to:

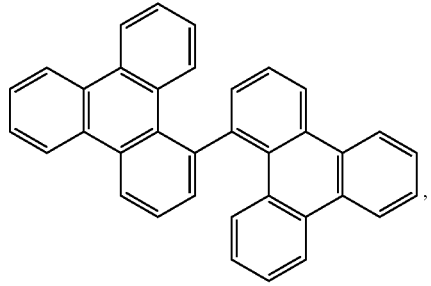

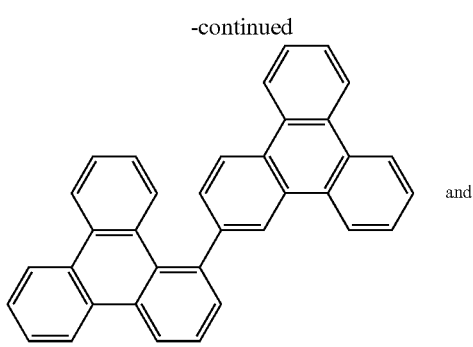

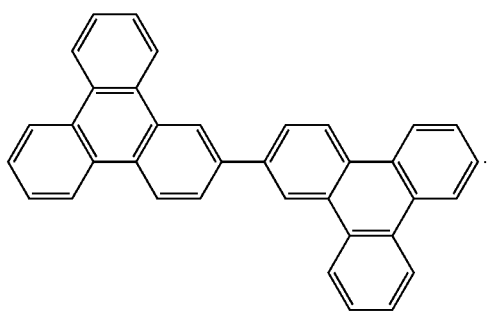

Compounds having a repeating unit containing a triphenylene moiety also include those where triphenylene moiety has the structure

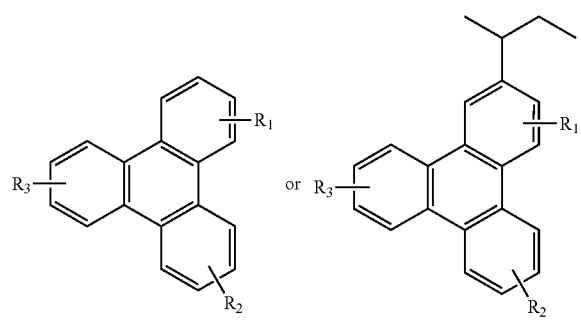

wherein $R_1$, $R_2$, and $R_3$ is each independently selected from the group consisting H, aryl, substituted aryl, heteroaryl, substituted heteroaryl, alkyl, arylkyl, heteroalkyl, alkenyl, and alkynyl.

Examples include but are not limited to those where the triphenylene moiety has the formula

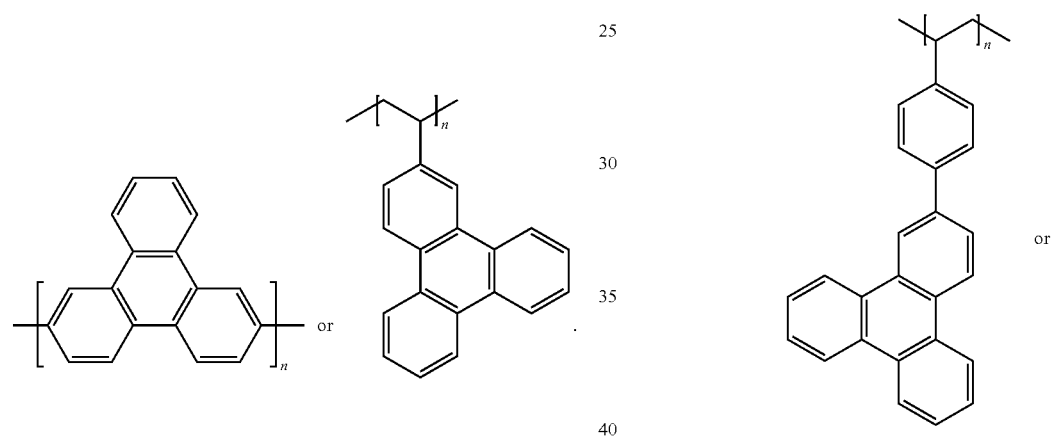

Where n>5

Compounds having a repeating unit containing a triphenylene moiety also include those where triphenylene moiety has the structure

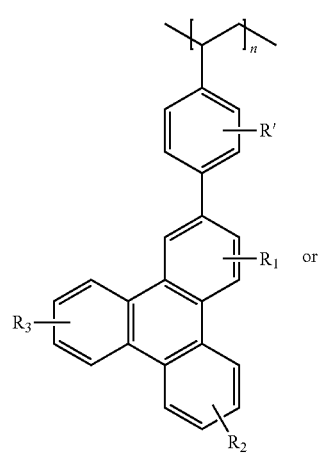

IX

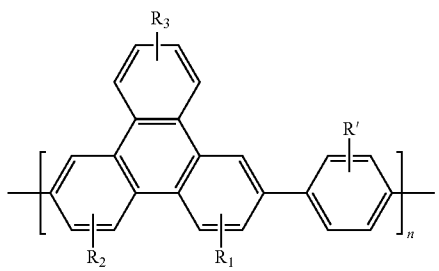

XI

Where n>5 and $R_1$, $R_2$, $R_3$ and R' is each independently selected from the group consisting of, aryl, substituted aryl, heteroaryl, substituted heteroaryl, alkyl, arylkyl, heteroalkyl, alkenyl, and alkynyl.

Examples include but are not limited to those where the triphenylene moiety has the formula

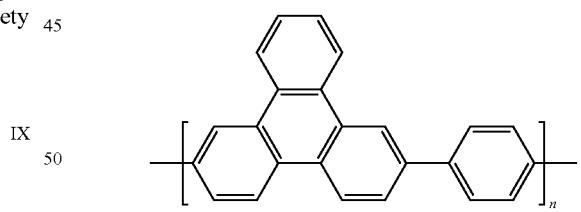

In another embodiment, the present invention provides an organic emissive layer comprising a phosphorescent material and a triphenylene compound, as well as a device including said emissive layer, wherein the triphenylene compound has a multi-benzotriphenylene structure. Preferred multi-benzotriphenylenes are those that can be evaporated at vacuum without decomposition. Examples include but are not limited to:

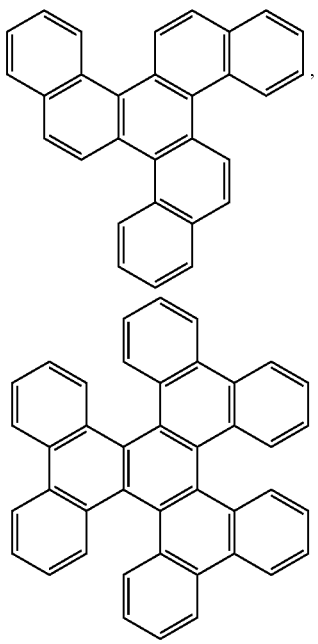

In another embodiment, the present invention provides an organic emissive layer comprising a phosphorescent material and a triphenylene compound, as well as a device including said emissive layer, wherein the triphenylene compound has a fused-triphenylenylene structure. Preferred fused-triphenylenylene structures include but are not limited to

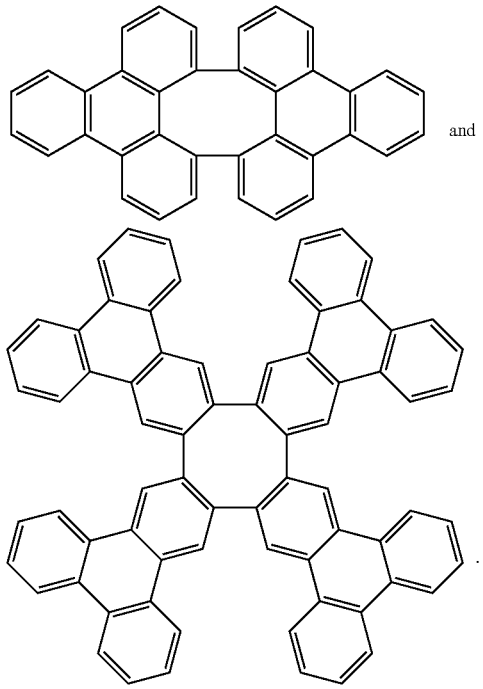

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting.

MATERIAL DEFINITIONS

As used herein, abbreviations refer to materials as follows:

CBP: 4,4'-N,N-dicarbazole-biphenyl m-MTDATA 4,4',4''-tris(3-methylphenylphenlyamino)triphenylamine $Alq_3$: 8-tris-hydroxyquinoline aluminum Bphen: 4,7-diphenyl-1,10-phenanthroline n-BPhen: n-doped BPhen (doped with lithium)

$F_4$-TCNQ: tetrafluoro-tetracyano-quinodimethane p-MTDATA: p-doped m-MTDATA (doped with $F_4$-TCNQ)

$Ir(ppy)_3$: tris(2-phenylpyridine)-iridium $Ir(ppz)_3$: tris(1-phenylpyrazoloto,N,C(2')iridium(III)

BCP: 2,9-dimethyl-4,7-diphenyl-1,10-phenanthroline

TAZ: 3-phenyl-4-(1'-naphthyl)-5-phenyl-1,2,4-triazole

CuPc: copper phthalocyanine.

ITO: indium tin oxide

NPD: N,N'-diphenyl-N—N'-di(1-naphthyl)-benzidine

TPD: N,N'-diphenyl-N—N'-di(3-toly)-benzidine

BAlq: aluminum(III)bis(2-methyl-8-hydroxyquinolinato)4-phenylphenolate mCP: 1,3-N,N-dicarbazole-benzene DCM: 4-(dicyanoethylene)-6-(4-dimethylaminostyryl-2-methyl)-4H-pyran DMQA: N,N'-dimethylquinacridone PEDOT:PSS: an aqueous dispersion of poly(3,4-ethylenedioxythiophene) with polystyrenesulfonate (PSS)

HPT: 2,3,6,7,10,11-hexaphenyltriphenylene 2,7-DCP 2,7-N,N-dicarbazolephenanthrene 3,3'-DC-o-TerP 3,3'-dicarbazole-o-terphenyl 4,4'-DC-o-TerP 4,4'-dicarbazole-o-terphenyl 2,6'-DCN 2,6-N,N-dicarbazolenaphthalene $Ir(5-Phppy)_3$ tris[5'-phenyl(2-phenylpyridine)]iridium(III)

$Ir(3-Meppy)_3$: tris(3-methyl-2-phenylpyridine) iridium(III)

$Ir(1-piq)_3$: tris(1-phenylisoquinoline)iridium(III)

$Ir(3-Mepq)_2(acac)$: bis[3-methyl-2-phenylquinoline)]iridium(III) acetylacetonate $Ir(5-Phppy)_3$: tris[5-phenyl(2-phenylpyridine)]iridium(III)

$Ir(pq)_2(acac)$: bis[2-phenylquinoline)]iridium(III) acetylacetonate 2,2-BT: 2,2-bistriphenylene HPT: 2,3,6,7,10,11-hexaphenyltriphenylene H1NT 2,3,6,7,10,11-hexa(1-naphthyl)triphenylene H2BT 2,3,6,7,10,11-hexa(2-biphenyl)triphenylene Specific representative embodiments of the invention will now be described, including how such embodiments may be made. It is understood that the specific methods, materials, conditions, process parameters, apparatus and the like do not necessarily limit the scope of the invention.

Synthesis of Multi-Aryl-Substituted Triphenylene Compounds

Synthesis of 2,3,6,7,10,11-hexaphenyltriphenylene (HPT)

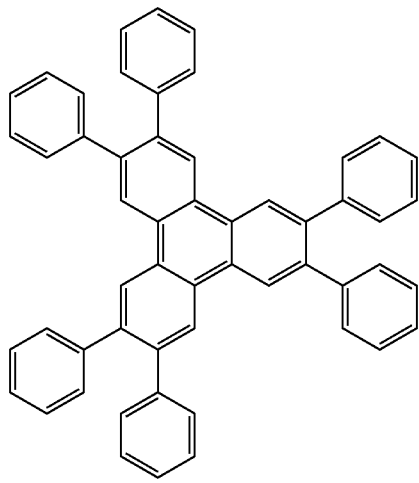 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1]

2,3,6,7,10,11-hexaphenyltriphenylene was synthesized according to US20050025993.

Synthesis of 2,3,6,7,10,11-hexa(4-t-butylphenyl)triphenylene (4-t-butylHPT)

Step 1. Preparation of 2,3,6,7,10,11-hexabromotriphenylene 2,3,6,7,10,11-Hexabromotriphenylene was prepared according to the literature method (Breslow et al, Tetrahedron, 1982, 38, 863). Triphenylene (3.0 g, 13.2 mmol) was dissolved in 70 mL of nitrobenzene. 0.27 g of Fe powder was added. To this mixture, bromine (18.6 g, 120 mmol) in 20 mL of nitrobenzene was added via a dropping funnel. The mixture was stirred at room temperature for 12 hours and brought to reflux for 2 hours. After cooling, the solid was filtered, washed with ethanol and dried. 8.9 g (96%) of crude product was obtained. Recrystallization in boiling 1,2-dichlorobenzene (~180° C.) yielded the product as off-white needles (8.64 g, 94%). The product was confirmed by mass spectrometry.

Step 2: Preparation of 2,3,6,7,10,11-hexa(4-t-butylphenyl)triphenylene (Compound VII)

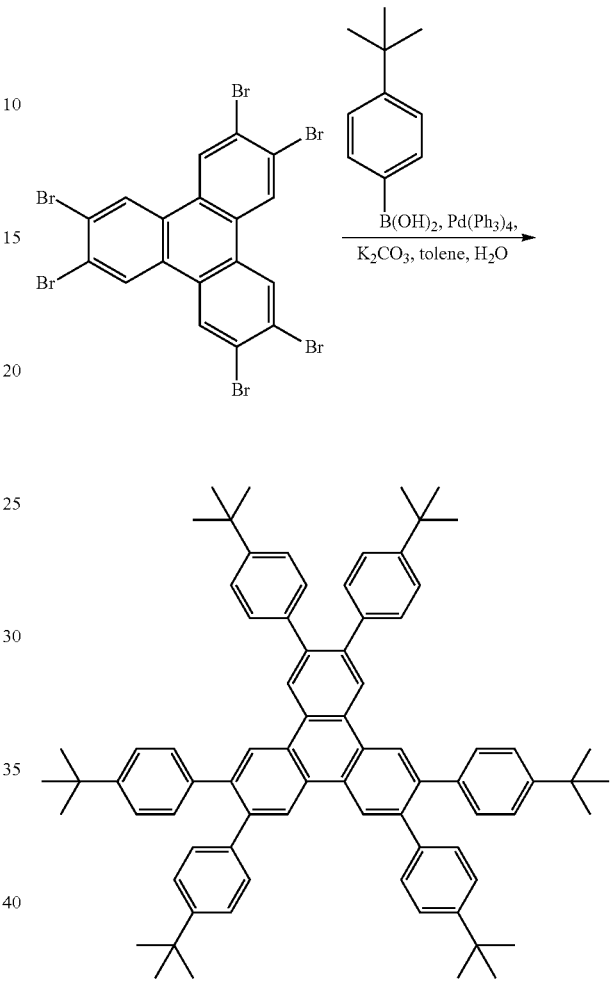

2,3,6,7,10,11-hexabromotriphenylene (8.64 g, 12.3 mmol), 4-t-butylphenylboronic acid (13.5 g, 111 mmol), triphenylphosphine (0.64 g, 2.46 mmol), Pd(OAc)$_2$ (0.14 g, 0.615 mmol), K$_2$CO$_3$ (20.4 g, 147.6 mmol) were in 600 mL of xylenes and 50 mL of water. The mixture was purged with nitrogen for 5 minutes and slowly brought to reflux under nitrogen. TLC (CH$_2$Cl$_2$:hexane ~1:2 v/v, the starting hexabromo compound did not move) showed the appearance of a new spot (xylenes also showed up on the TLC but it eluted up faster than the product) within hours. The mixture was refluxed for 12 hours. After cooling, the solid was filtered, washed with ethanol and dried. The crude yield was higher than 90%. Recrystallization in xylenes (~100 mL per 3-4 g of product) yield white crystals. Vacuum sublimation yielded the product (~4.5 g) which was confirmed by NMR and mass spectrometry. This material is very soluble in common organic solvents and can be used in solution processed devices. For example, a 1% by weight solution of 4-t-butyl- HPT in toluene can be spin-coated on silicon wafer at 1000 and 2000 rpm to give uniform films of ~60 and ~40 nm in thickness respectively.

Synthesis of
2,3,6,7,10,11-hexa(2-naphthyl)triphenylene (H2NT)

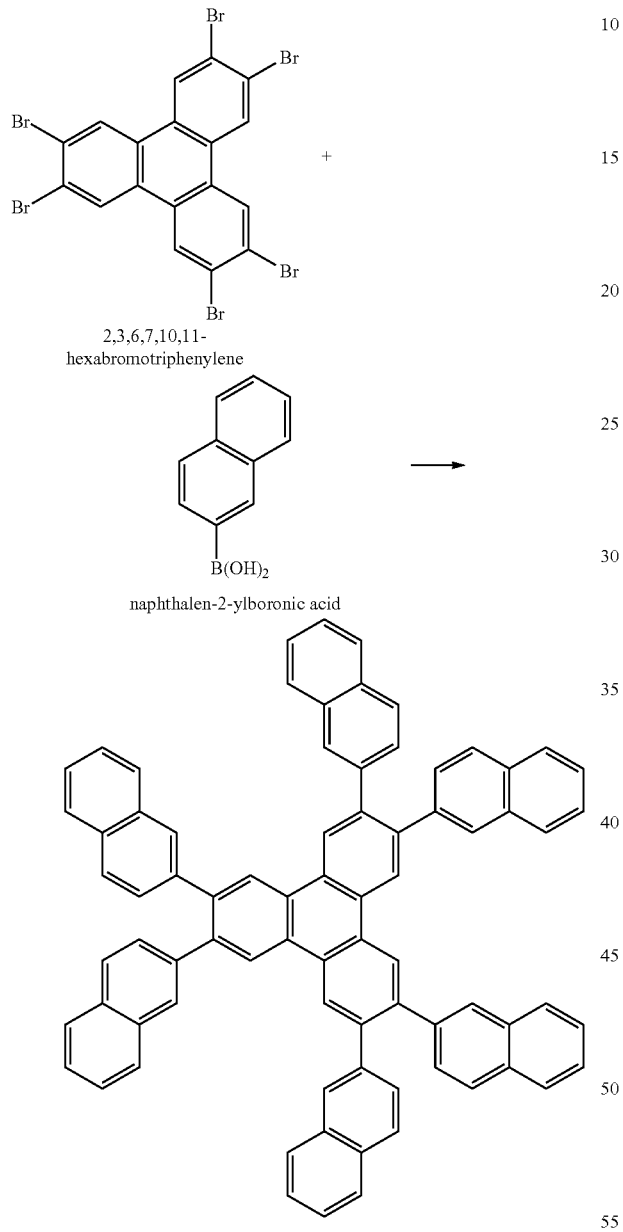

2.0 g of 2,3,6,7,10,11-hexabromotriphenylene (2.85 mmol), 4.4 g of naphthalene-2-ylboronic acid (25.6 mmol), 0.15 g triphenylphosphine (0.57 mmol), 0.03 g Palladium acetate (0.14 mmol) was placed in a 3-neck 1 L round bottomed flask. 250 mL of xylenes was then added followed by 250 ml of a 0.1M Potassium carbonate solution. The mixture was thoroughly degassed by bubbling nitrogen for 30 mins. The mixture was then refluxed for 24 hours in a nitrogen atmosphere. The reaction was then allowed to cool and the contents transferred to a separatory funnel. The aqueous layer was removed and the organic layer was washed with water. The organic layer was dried over magnesium sulphate and then the solvent removed in vacuo. The product was purified using column chromatography with dichlormethane/hexanes (50/50) as the mobile phase.

Synthesis of
2,3,6,7,10,11-hexa(1-naphthyl)triphenylene (H1NT)

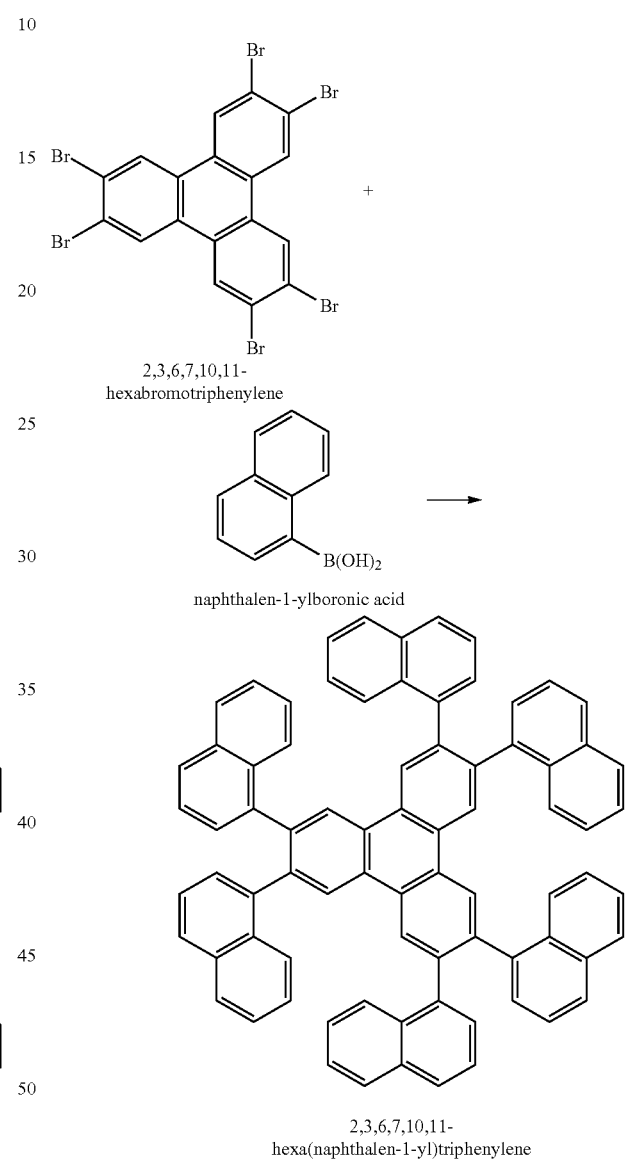

2.0 g of 2,3,6,7,10,11-hexabromotriphenylene (2.80 mmol), 4.4 g of naphthalene-1-ylboronic acid (25.6 mmol), 0.22 dicyclohexyl(2',6'-dimethoxybiphenyl-2-yl)phosphine (0.5 mmol), 0.14 g tris dibenzylidene acetone palladium(0) (0.15 mmol) was placed in a 3-neck 1 L round bottomed flask. 250 mL of xylenes was then added followed by 250 ml of a 0.1M Potassium phosphate tribasic solution. The mixture was thoroughly degassed by bubbling nitrogen for 30 mins. The mixture was then refluxed for 24 hours in a nitrogen atmosphere. The reaction was then allowed to cool and the contents transferred to a separatory funnel. The aqueous layer was removed and the organic layer was washed with water. The organic layer was dried over magnesium sulphate and

Synthesis of 2,3,6,7,10,11-hexa(biphenyl-2-yl)triphenylene (H2BT)

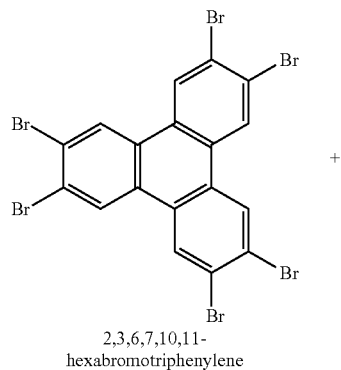

2,3,6,7,10,11-hexabromotriphenylene

+

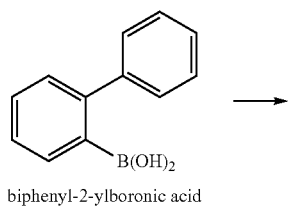

biphenyl-2-ylboronic acid

→

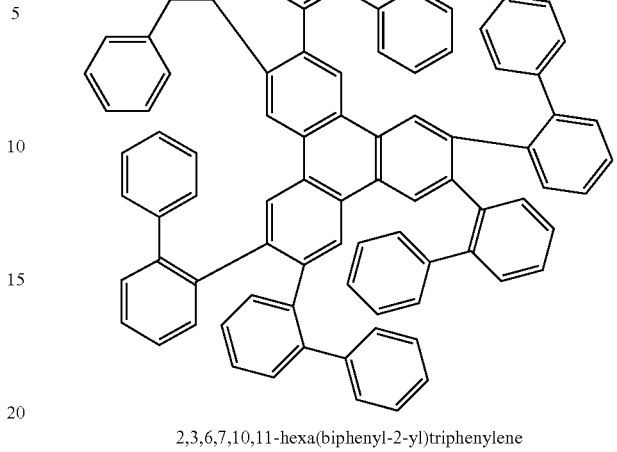

2,3,6,7,10,11-hexa(biphenyl-2-yl)triphenylene 1.0 g of 2,3,6,7,10,11-hexabromotriphenylene (1.4 mmol), 2.5 g of biphenyl-2-ylboronic acid (25.6 mmol), 0.11 dicyclohexyl(2',6'-dimethoxybiphenyl-2-yl)phosphine (0.26 mmol), 0.07 g tris dibenzylidene acetone palladium(0) (0.076 mmol) was placed in a 3-neck 1 L round bottomed flask. 250 mL of xylenes was then added followed by 250 ml of a 0.1M Potassium phosphate tribasic solution. The mixture was thoroughly degassed by bubbling nitrogen for 30 mins. The mixture was then refluxed for 24 hours in a nitrogen atmosphere. The reaction was then allowed to cool and the contents transferred to a separatory funnel. The aqueous layer was removed and the organic layer was washed with water. The organic layer was dried over magnesium sulphate and then the solvent removed in vacuo. The product was purified using column chromatography with dichlormethane:hexanes (50:50) as the mobile phase.

The other multi-aryl-substituted triphenylene examples can be synthesized by one skilled in the art via Suzuki coupling with the corresponding halotriphenylene and arylboronic acids.

Electrochemistry of triphenylene and 2,3,6,7,10,11-hexaaryltriphenylene is summarized in the Table 1.

TABLE 1

| Compound | Structure | $E_{ox}$ (V) vs Fc/Fc$^+$ in DMF | $E_{red}$ (V) vs Fc/Fc$^+$ in DMF |
| --- | --- | --- | --- |
| triphenylene | 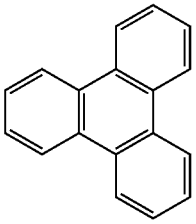 [SMILES: c1ccc2c(c1)c1ccccc1c1ccccc21] | Not observed up to 1.0 | −3.0 |

TABLE 1-continued

| Compound | Structure | $E_{ox}$ (V) vs Fc/Fc$^+$ in DMF | $E_{red}$ (V) vs Fc/Fc$^+$ in DMF |
|---|---|---|---|
| 2,2-BT | 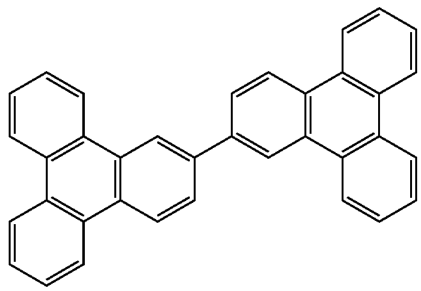 [SMILES: c1ccc2c(c1)c1ccccc1c1cc(-c3ccc4c5ccccc5c5ccccc5c4c3)ccc21] | 1.0 (irreversible) | −2.6 |
| HPT | 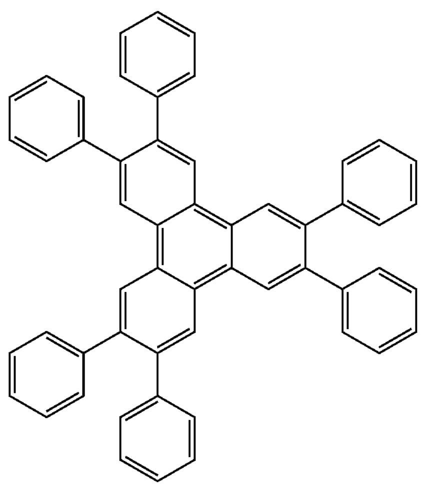 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | Not observed up to 1.0 | −2.6 |
| H2NT | 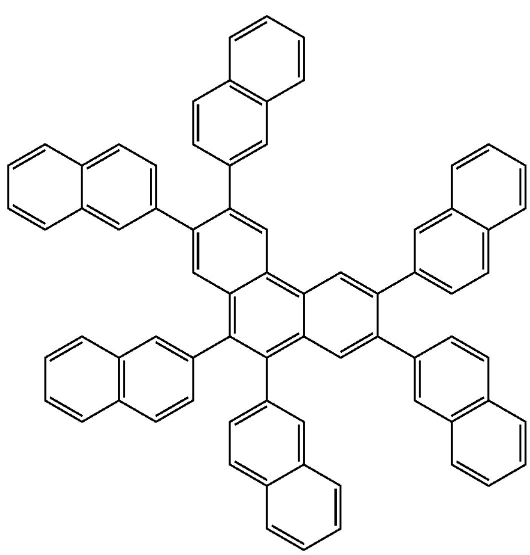 [SMILES: c1ccc2cc(-c3cc4c(-c5ccc6ccccc6c5)c(-c5ccc6ccccc6c5)c5cc(-c6ccc7ccccc7c6)c(-c6ccc7ccccc7c6)cc5c4cc3-c3ccc4ccccc4c3)ccc2c1] | 1.0 (irreversible) | −2.5 |

TABLE 1-continued
| Compound | Structure | $E_{ox}$ (V) vs Fc/Fc$^+$ in DMF | $E_{red}$ (V) vs Fc/Fc$^+$ in DMF |
|---|---|---|---|
| H1NT | 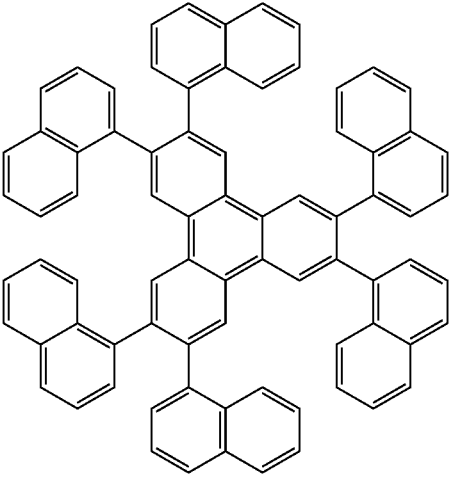 [SMILES: c1ccc2c(-c3cc4c5cc(-c6cccc7ccccc67)c(-c6cccc7ccccc67)cc5c5cc(-c6cccc7ccccc67)c(-c6cccc7ccccc67)cc5c4cc3-c3cccc4ccccc34)cccc2c1] | 1.0 (irreversible) | −2.6 |
| H2BT | 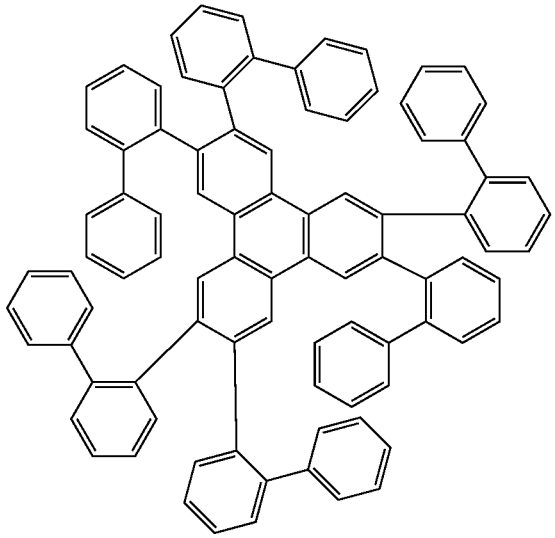 [SMILES: c1ccc(-c2ccccc2-c2cc3c4cc(-c5ccccc5-c5ccccc5)c(-c5ccccc5-c5ccccc5)cc4c4cc(-c5ccccc5-c5ccccc5)c(-c5ccccc5-c5ccccc5)cc4c3cc2-c2ccccc2-c2ccccc2)cc1] | Not observed up to 1.0 | −2.7 |

Synthesis of Compounds Having a Triphenylene Repeat Unit

Triphenylenylene Compounds

Synthesis of 2,2-Bistriphenylene (2,2-BT)

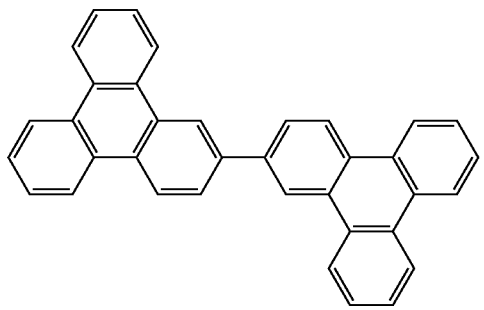 [SMILES: c1ccc2c(c1)c1ccccc1c1cc(-c3ccc4c5ccccc5c5ccccc5c4c3)ccc21]

2,2-Bistriphenylene was synthesized according to Organic Letters 2001, 3, 811. and UA20040076852A1

Synthesis of 1,1-Bistriphenylene (1,1-BT)

1,1-Bistriphenylene can be synthesized according to Organometallics, 2004, 23, 3079

Arylenetriphenylene Compounds

Synthesis of 1,3-bis(triphenylen-2-yl)benzene

Step 1: Synthesis of 2-bromotriphenylene

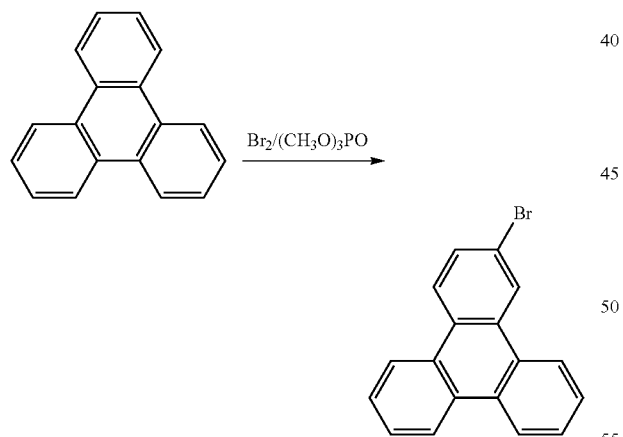

3.2 g (14 mmol) of triphenylene was dissolved in 60 mL of trimethyl phosphate. To the suspension was added 2.23 g (14 mmol) of bromine in 10 mL of trimethyl phosphate at room temperature under $N_2$. The mixture was then heated up to 80° C. The reaction was monitored by HPLC. The reaction was quenched by pouring into ice water, then extracted with dichloromethane and washed with saturated sodium bisulfite solution. After drying with magnesium sulfate, the solvent was evaporated. The crude product was run through a short silica gel plug using dichloromethane. 3.0 g of product was obtained after drying under vacuum. The product contains triphenylene, 1-bromotriphenylene, 2-bromotriphenylene, and a mixture of dibromotriphenylene isomers.

Step 2: Synthesis of 4,4,5,5-tetramethyl-2-(triphenylen-2-yl)-1,3,2-dioxaborolane

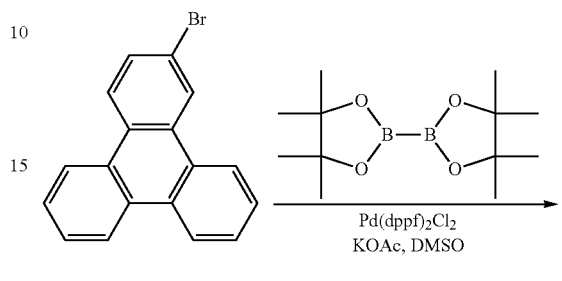

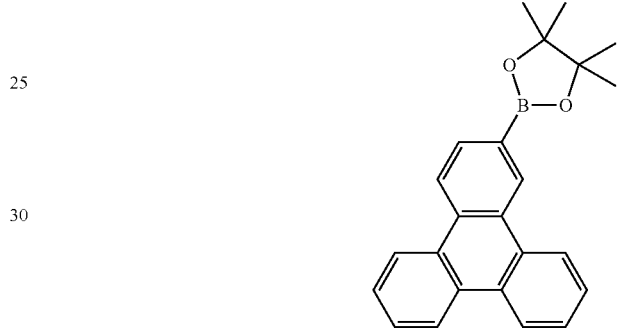

3.0 g of the bromotriphenylene mixture, 2.8 g (11 mmol) of bis(pinacolato)diboron, 0.24 g of $Pd(dppf)_2Cl_2$, 3.0 g (30 mmol) of potassium acetate, and 60 mL of DMSO was mixed at room temperature under $N_2$. The mixture was degassed before heated up to 80° C. for 14 hours. After cooling to room temperature, the mixture was poured into ice water. The precipitate was then collected by filtration. The solid was dissolved in ether and dried over magnesium sulfate. The crude product was purified by column using a mixture of hexanes and dichloromethane as eluent. 1.3 g of pure product was isolated.

Step 3: Synthesis of 1,3-bis(triphenylen-2-yl)benzene

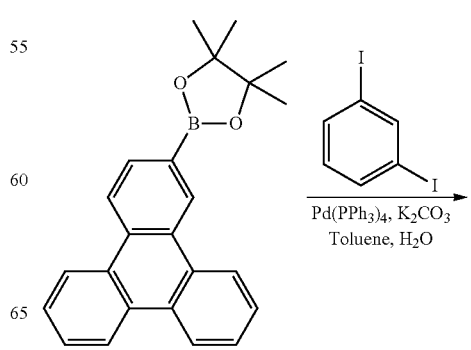

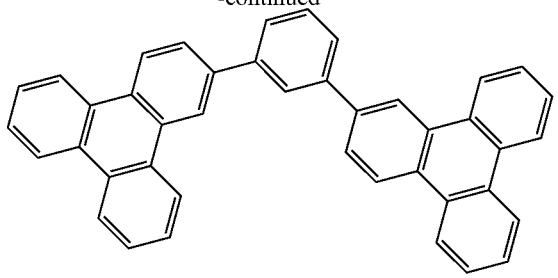

1.23 g (3.5 mmol) of the triphenylene boronic ester from the previous step, 0.5 g (1.5 mmol) of 1,3-diiodobenzene, 1.0 g (7.5 mmol) of potassium carbonate, 30 mL of toluene, and 10 mL of water was mixed in a 250 mL three-neck flask. The system was purged by nitrogen for 10 min before adding 0.05 g of Pd(PPh$_3$)$_4$. The mixture was then heated up to 87° C. with vigorous stirring. After 24 hr, to the mixture was added 200 mL of methanol. The precipitate was collected by filtration. The solid was washed with copious amount of methanol, then hexanes. The solid was then recrystallized from 80 ml of xylenes. Final purification of the product involved subliming the material at 250° C. 0.35 g product was collected as white needle crystals.

Synthesis of 3,3'-bis(triphenylen-2-yl)biphenyl

Step 1: Synthesis of 2-aminotriphenylene 3.1 g (11.3 mmol) of a mixture of 1 and 2-nitrotriphenylene (synthesized according to J. Chem. Soc., 1955, 4482) in about 100 mL of ethanol, 600 mg (0.57 mmol) of Pd/C (10% on activated carbon), and 2.3 g (45.2 mmol) of hydrazine monhydride were charged in a 250 mL round bottle flask. The reaction mixture was heated up to reflux under nitrogen for 2 hours. The reaction mixture was then filtered and the filtrate was concentrated and passed through a silica gel column using 25% ethyl acetate in hexanes as elute. 1 and 2 aminotriphenyl were separated and confirmed by MS and NMR. This reaction yield was 100%.

Step 2: Synthesis of 2-bromotriphenylene

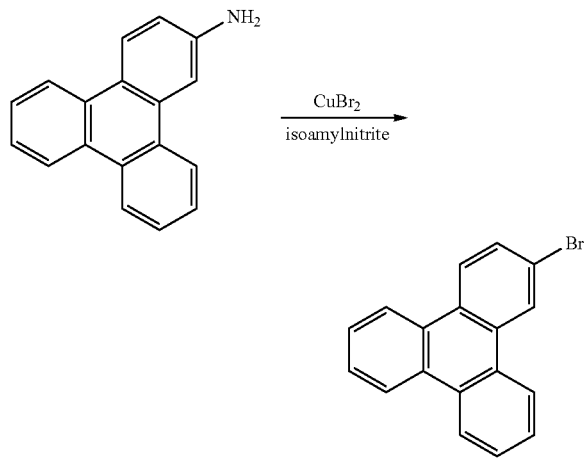

0.5 g (2.05 mmol) of 2-aminotriphenylene and 0.24 g (1.02 mmol) of anhydrous copper(II) bromide was placed in a 100 mL round bottomed flask. The flask was purged with nitrogen and evacuated several times. 25 mL of anhydrous acetonitrile was added to the solid. The flask was then placed in an ice/salt bath (−5° C.). 0.27 mL of isoamylnitrite was added dropwise to the solution through the septum. After all the isoamylnitrite was added, the mixture was stirred for two hours. The flask was then removed from the ice bath and stirred at room temperature for one hour followed by heating at 55° C. for 2 hours. The mixture was then cooled, the solvent removed in vacuo and the product column chromatographed using hexanes/dichloromethane (10%/90%) to give 0.36 g (60%) of the product.

Step 3: Synthesis of 3,3'-bis(triphenylen-2-yl)biphenyl

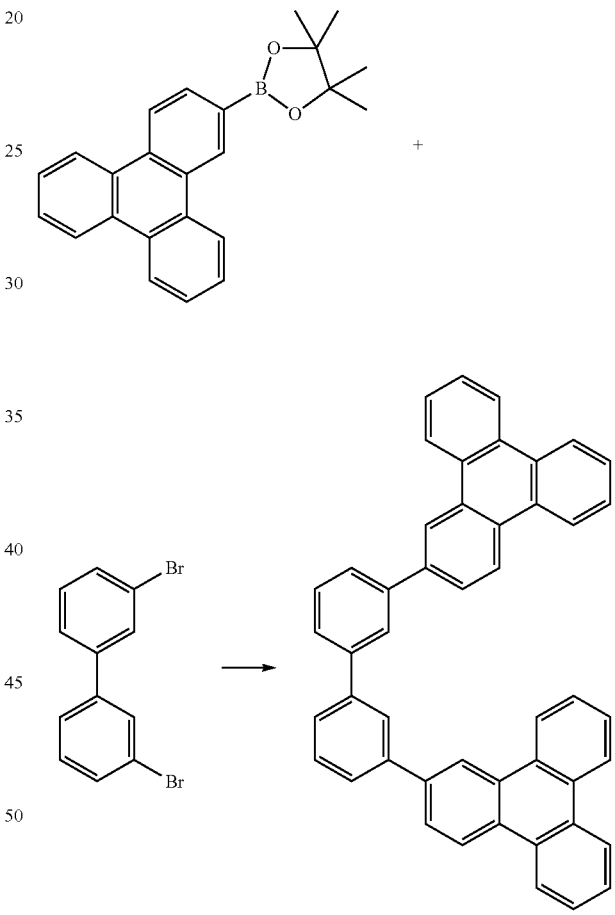

0.1 g (0.32 mmol) of 3,3'-dibromobiphenyl, 0.24 g (0.66 mmol) of 4,4,5,5-tetramethyl-2-(triphenylen-2-yl)-1,3,2-dioxaborolane, 0.03 g (0.07 mmol) of 2-dicyclohexylphosphino-2',6'-dimethoxybiphenyl (S-Phos) and 0.01 g (0.01 mmol) of tris(dibenzylideneacetone) palladium(0) was placed in a 3-neck 100 mL round-bottomed flask. 20 mL of xylenes and 20 ml of 3M potassium phosphate tribasic monohydrate solution was then added to the mixture. The biphasic solution was thoroughly purged with nitrogen for half an hour. The mixture was refluxed for 18 hours. Upon cooling the product precipitated. The product was filtered and washed with water. The product was then dissolved in dichlo-

Synthesis of Arylenetriphenylene Triphenylene Compound Having the Structure

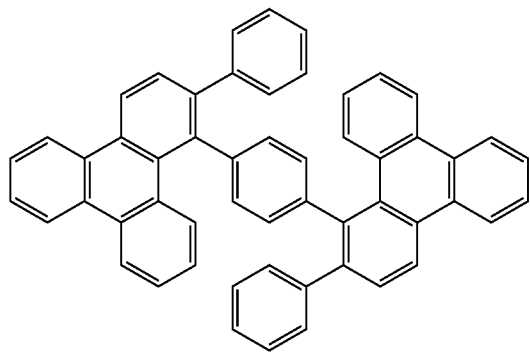 [SMILES: c1ccc(-c2ccc3c4ccccc4c4ccccc4c3c2-c2ccc(-c3c(-c4ccccc4)ccc4c5ccccc5c5ccccc5c34)cc2)cc1]

The compound having the structure above can be synthesized according to Angew. Chem., Int. Ed. Engl., 1996, 35, 886.

The other triphenylenylene and arylenetriphenylene examples can be synthesized by one skilled in the art via the coupling of 1 or 2-bromotriphenylene and 4,4,5,5-tetramethyl-2-(1 or 2-triphenylene)-1,3,2-dioxaborolane which can be prepared according to the aforementioned synthetic schemes.

Triphenylene Polymers

Preparation of: poly(2-vinyltriphenylene)

Poly(2-vinyltriphenylene) can be synthesized by the following scheme based on synthetic chemistry commonly used by those skilled in the art.

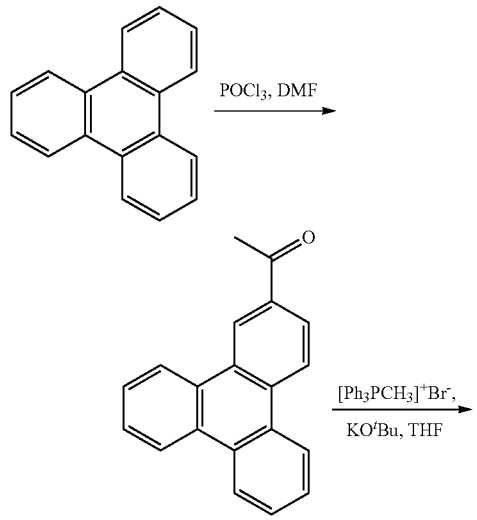

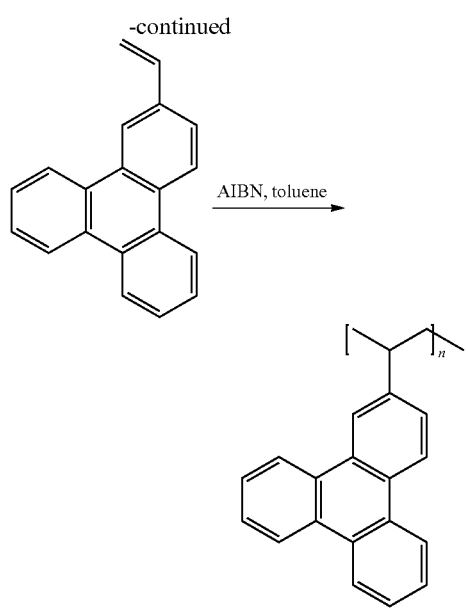

Synthesis of poly[2-(4-vinylphenyl)triphenylene]

Poly[2-(4-vinylphenyl)triphenylene] can be synthesized according to following scheme based on synthetic chemistry commonly used by those skilled in the art.

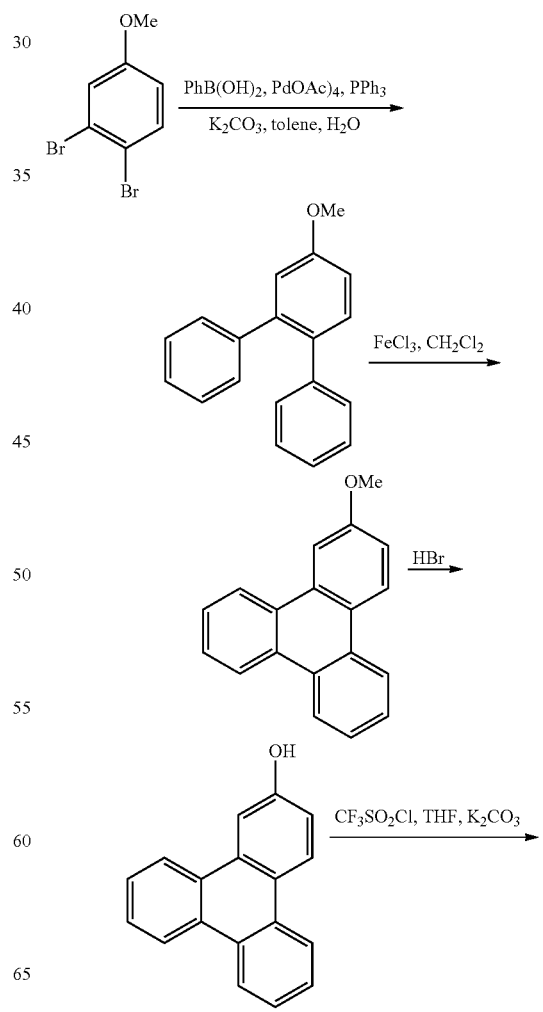

-continued

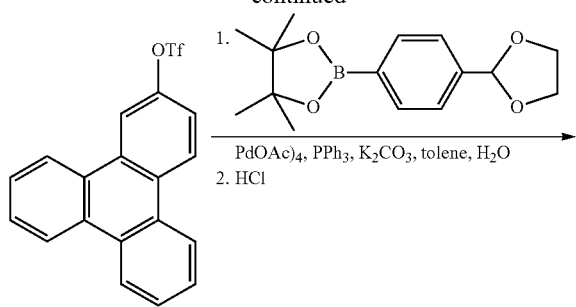

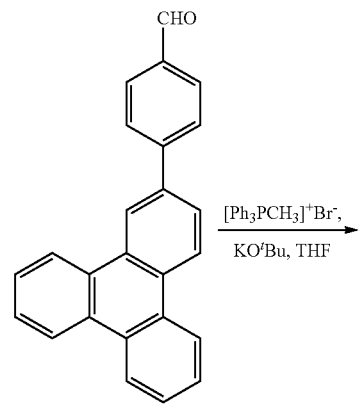

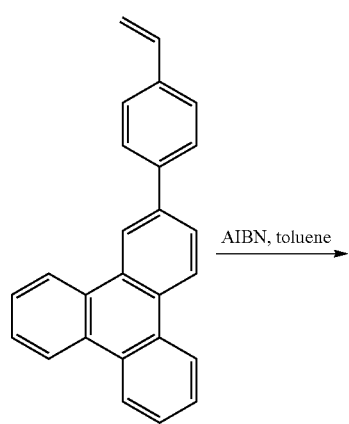

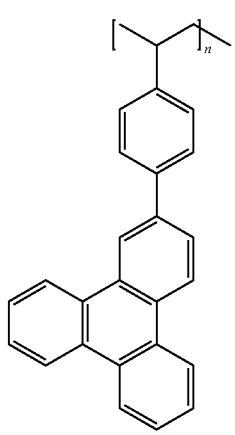

Synthesis of poly(2,7-triphenylene)

Poly(2,7-triphenylene) can be synthesized according to following scheme based on synthetic chemistry commonly used by those skilled in the art.

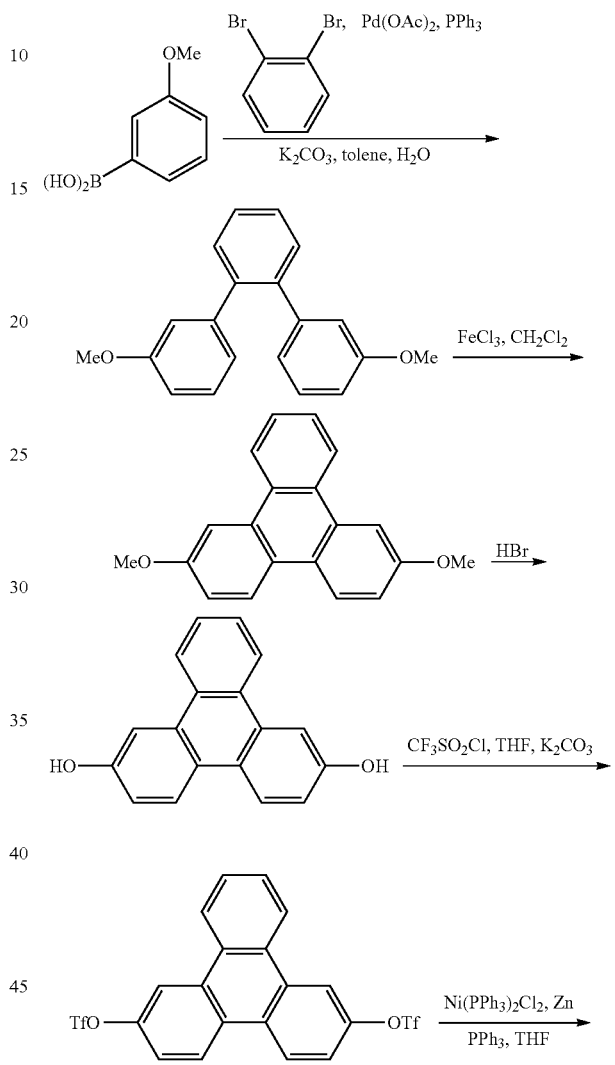

Synthesis of poly(2,7-triphenylenylene-1,4-phenylene)

Poly(2,7-triphenylenylene-1,4-phenylene can be synthesized according to following scheme based on synthetic chemistry commonly used by those skilled in the art.

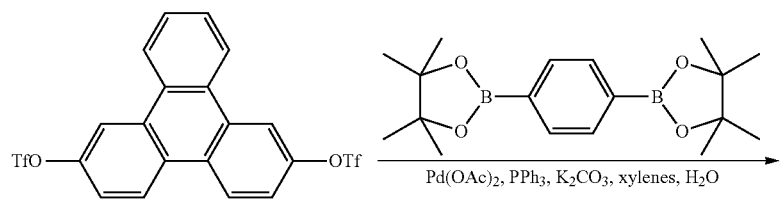

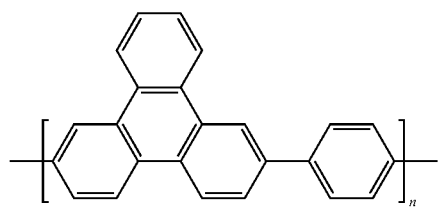

Synthesis of Benzotriphenylenylene Triphenylene Compounds

Synthesis of Benzotriphenylenylene Triphenylene Compound Having the Structure

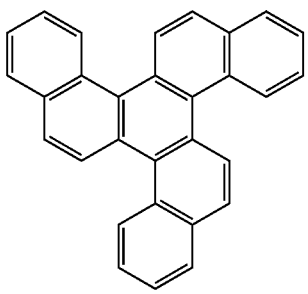 [SMILES: c1ccc2c(c1)ccc1c2c2ccc3ccccc3c2c2ccc3ccccc3c12]

The compound having the structure above can be synthesized according to J. Org. Chem., 1996, 61, 7198.

Synthesis of Benzotriphenylenylene Triphenylene Compound Having the Structure

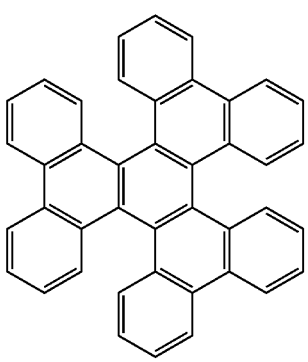 [SMILES: c1ccc2c(c1)c1ccccc1c1c2c2c3ccccc3c3ccccc3c2c2c3ccccc3c3ccccc3c12]

The compound having the structure above can be synthesized according to Org. Lett., 2000, 2, 1629.

Synthesis of Fused Triphenylene Compounds

Synthesis of 1,12-fused-bistriphenylene (1,12-fused-BT)

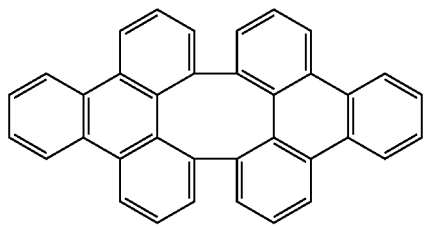

1,12-fused-BT 1,12-fused-bistriphenylene can be synthesized according to Organometallics, 2004, 23, 3079.

Synthesis of 1,12-fused-tetratriphenylene (1,12-fused-TT)

1,12-fused-tetratriphenylene may be synthesized according to following scheme.

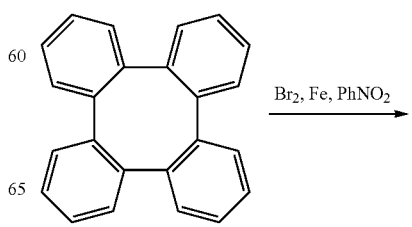

-continued

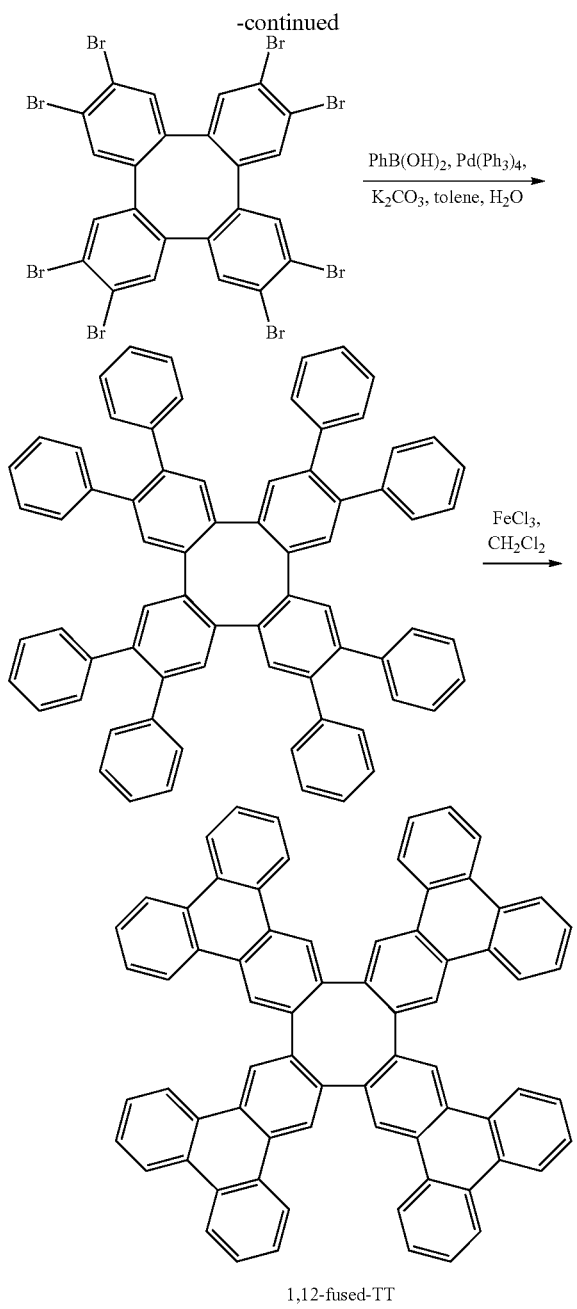

1,12-fused-TT

It is understood by those skilled in the art that substituted precursors can be used to synthesize substituted triphenylene products which may offer different properties than unsubstituted analogs such as higher solubility, lower evaporation temperature, higher/lower HOMO/LUMO energy levels which may be advantageous in specific device fabrication, architecture and application.

Device Fabrication and Measurement

All devices were fabricated by high vacuum (<10$^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

Device Examples 1-23 and Comparative Examples 1-6

Figure 17:
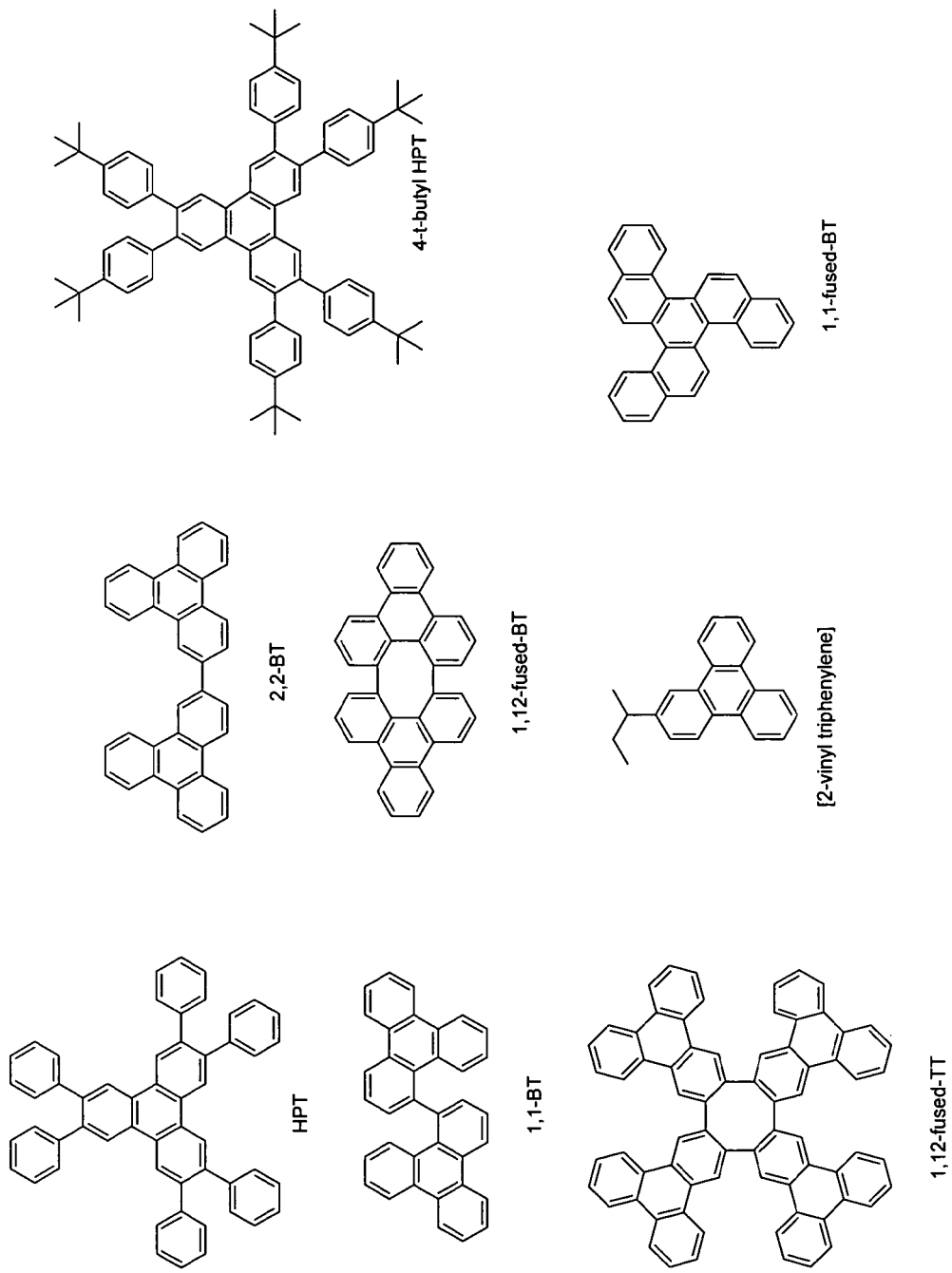
FIG. 17 shows chemical structures for HPT, 2,2-BT; 1,1-BT 1,1-fused-BT; 1,12-fused TT; 2-vinyltriphenylene and 4 t-butyl-HPT.
Figure 19:
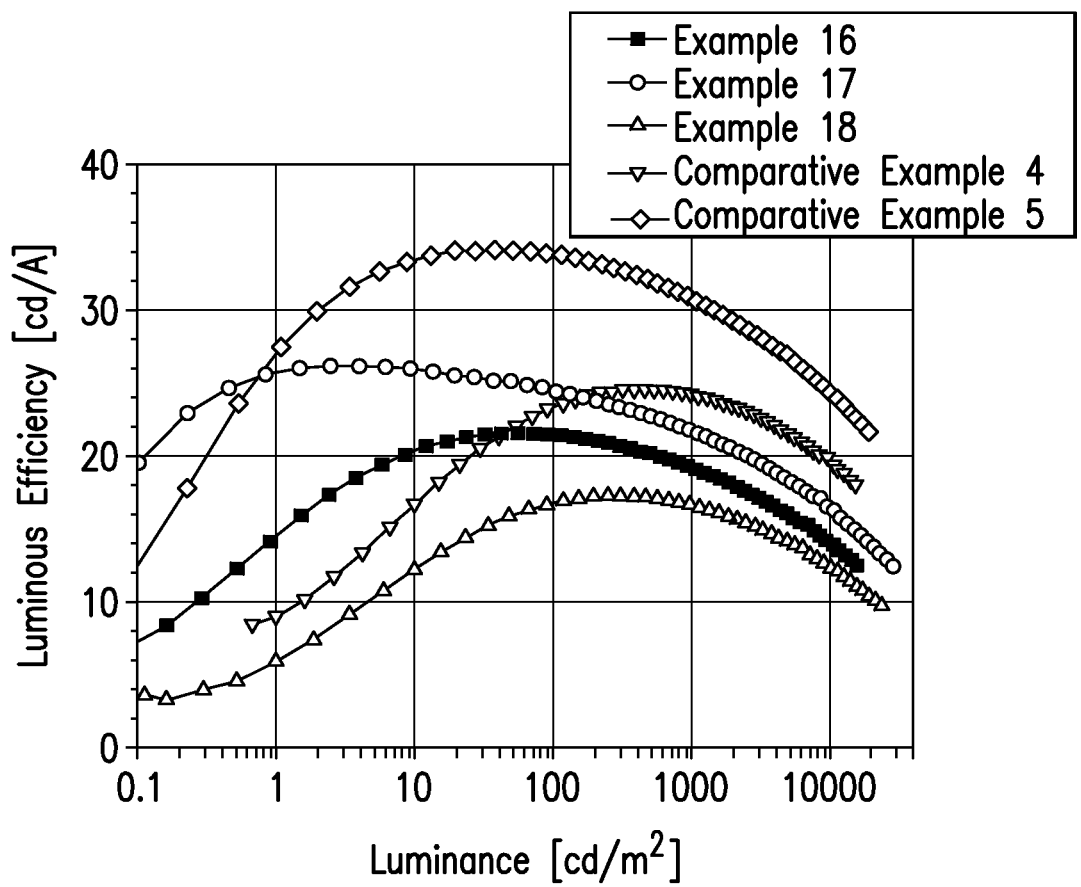
FIG. 19 shows luminous efficiency vs luminance of 2,2-BT:Ir(pq)$_2$(acac) devices.
Figure 20:
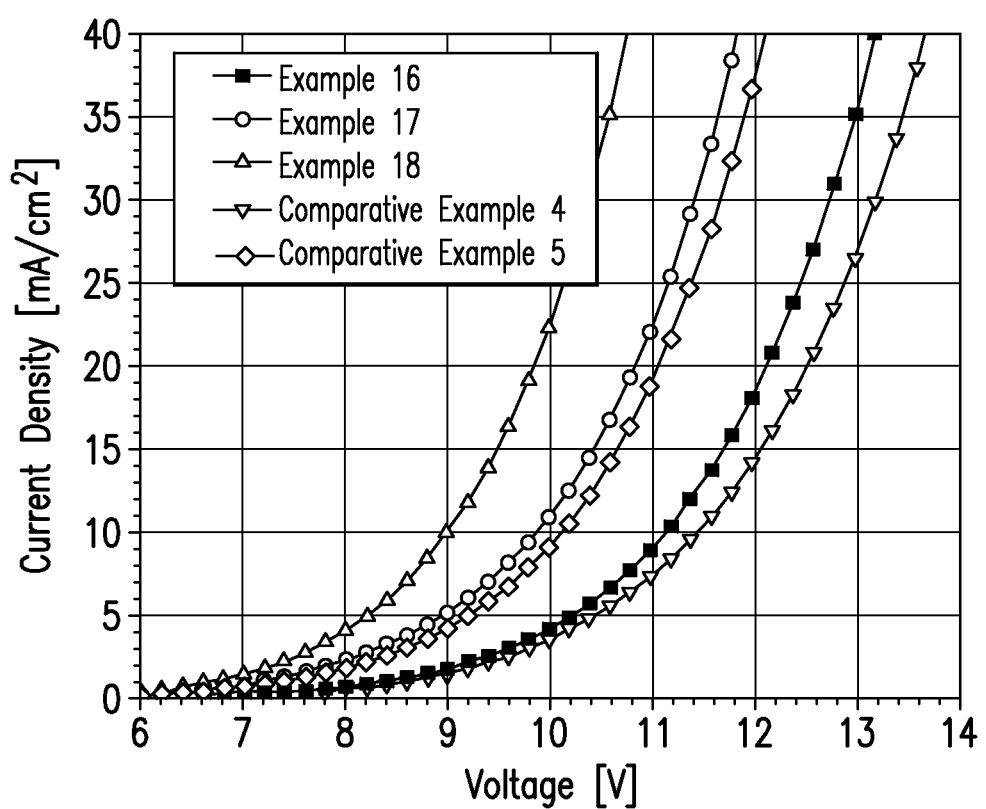
FIG. 20 shows current density vs voltage of 2,2-BT:Ir(pq)$_2$(acac) devices.
Figure 21:
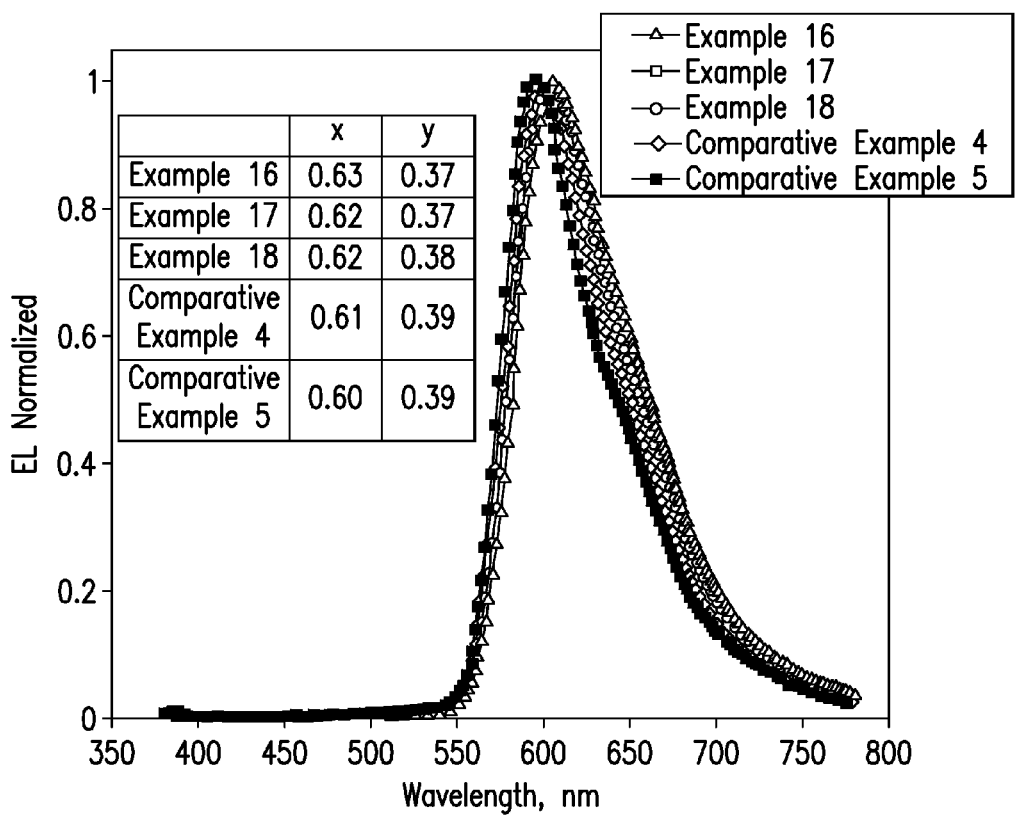
FIG. 21 shows EL and CIE of 2,2-BT:Ir(pq)$_2$(acac) devices at 10 mA/cm$^2$.
Figure 22:
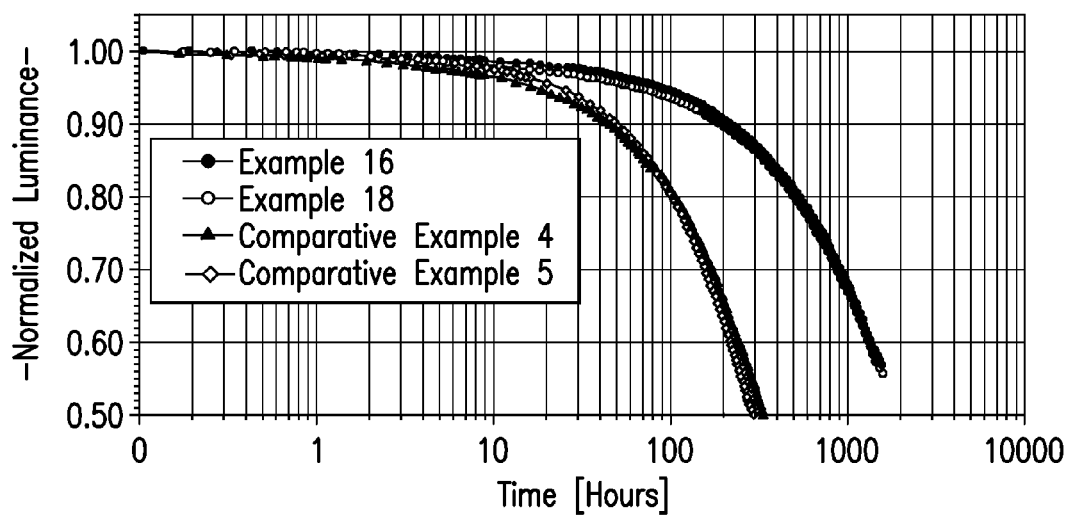
FIG. 22 shows lifetime of 2,2-BT:Ir(pq)$_2$(acac) devices.
Figure 23:
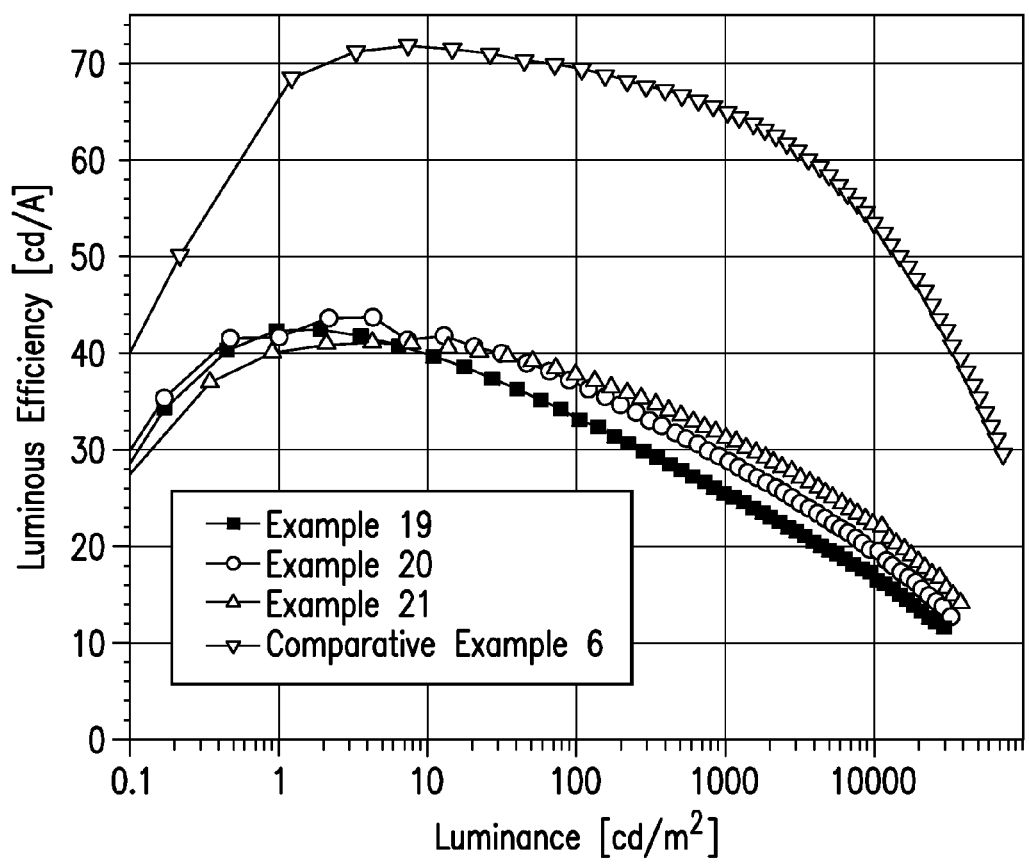
FIG. 23 shows luminous efficiency vs luminance of 2,2-BT:Ir(5-Phppy)$_3$ devices.
Figure 24:
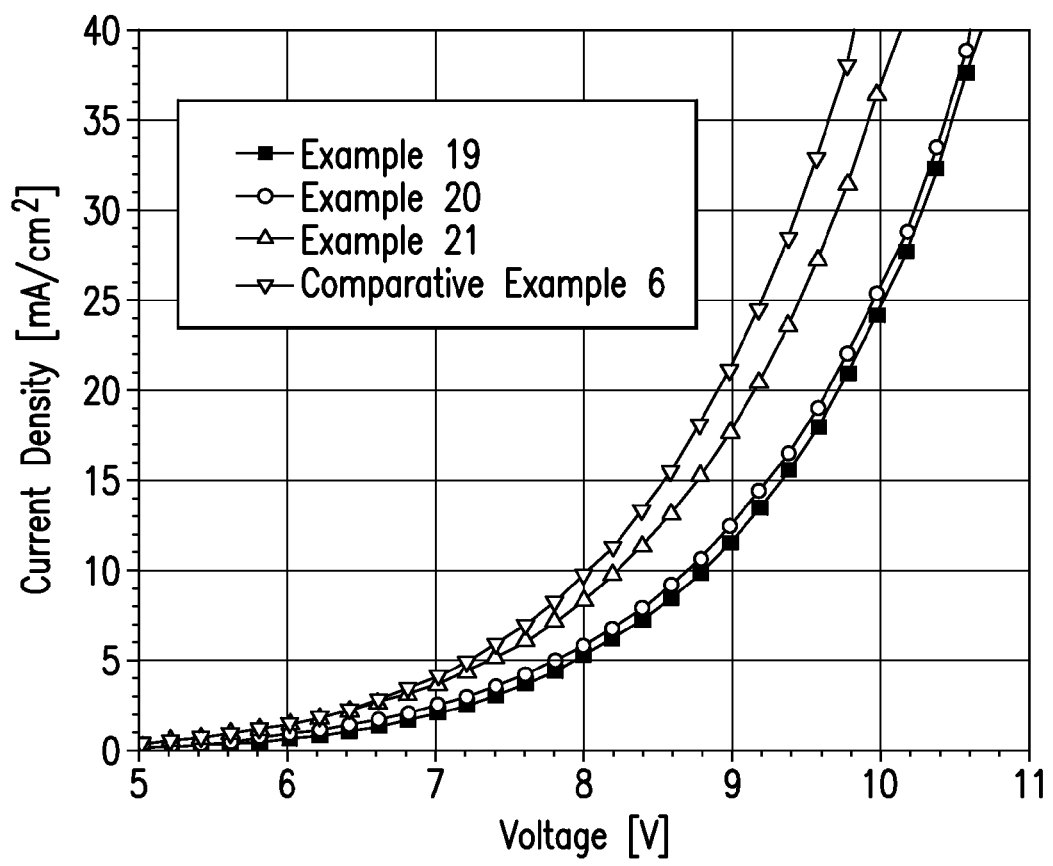
FIG. 24 shows current density vs voltage of 2,2-BT:Ir(5-Phppy)$_3$ devices.
Figure 25:
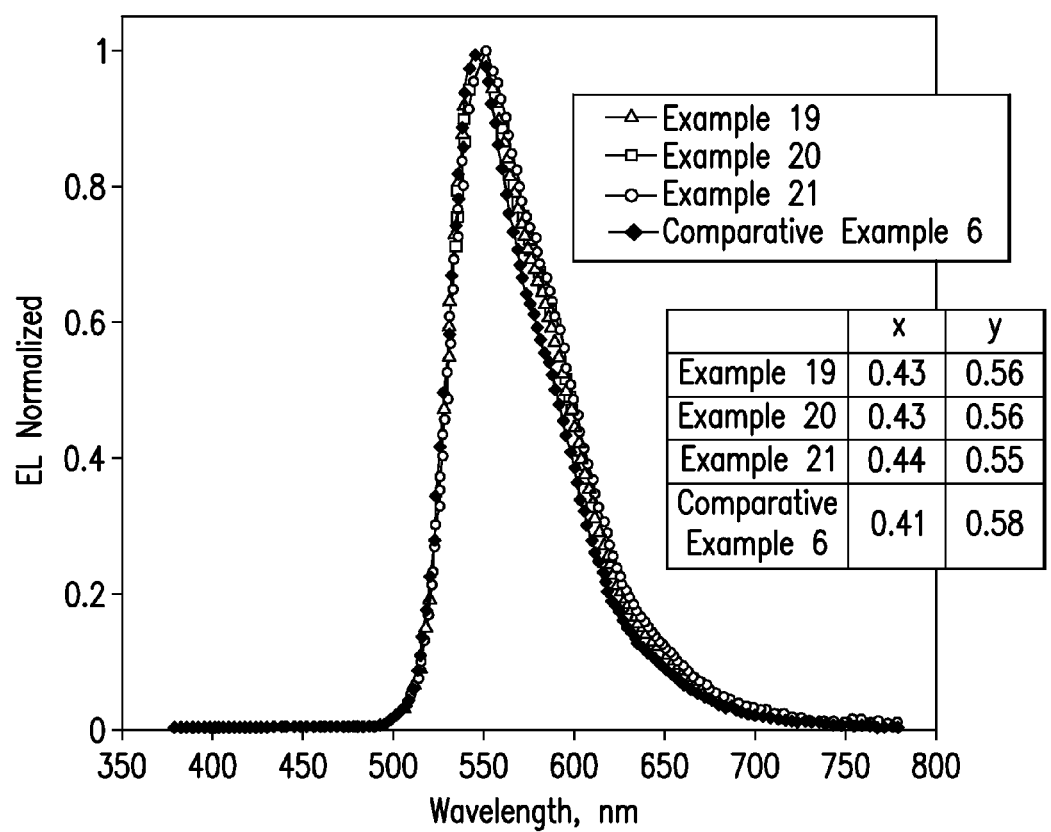
FIG. 25 shows EL and CIE of 2,2-BT:Ir(5-Phppy)$_3$ devices at 10 mA/cm$^2$.
Figure 26:
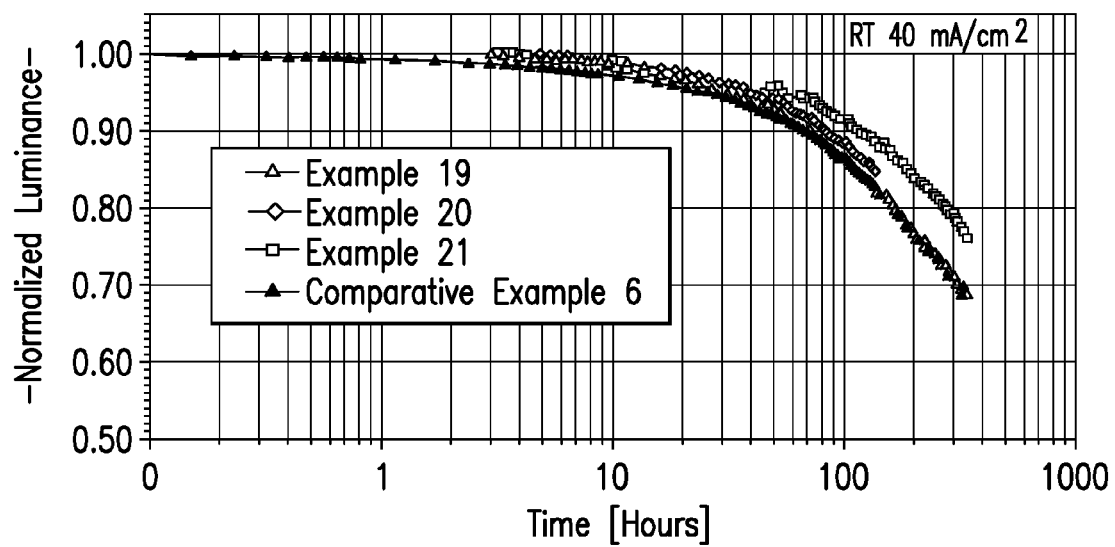
FIG. 26 shows lifetime of 2,2-BT:Ir(5-Phppy)$_3$ devices
Figure 28:
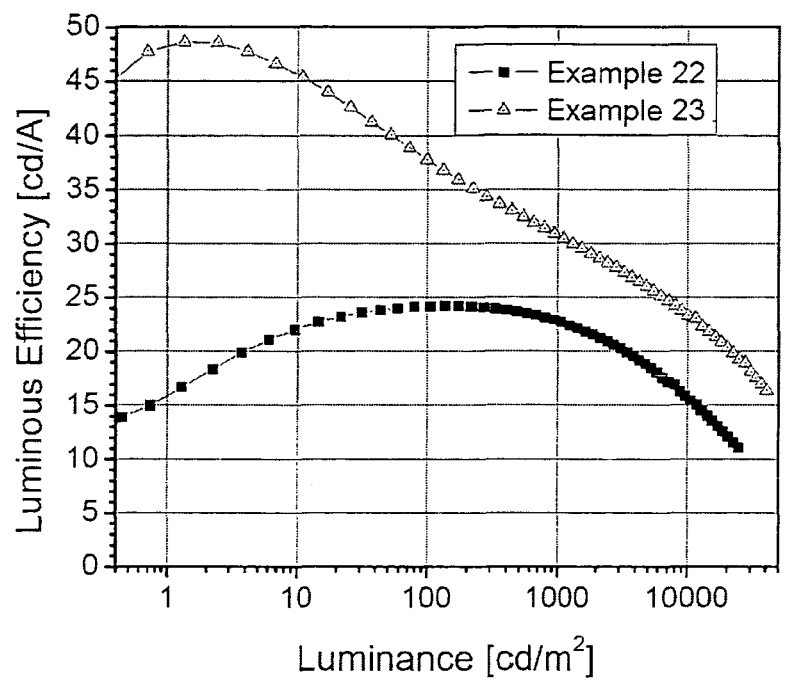
FIG. 28 shows luminous efficiency vs luminance of H1NT:Ir(pq)$_2$(acac) and H2BT:Ir(3-Meppy)$_3$ devices.
Figure 29:
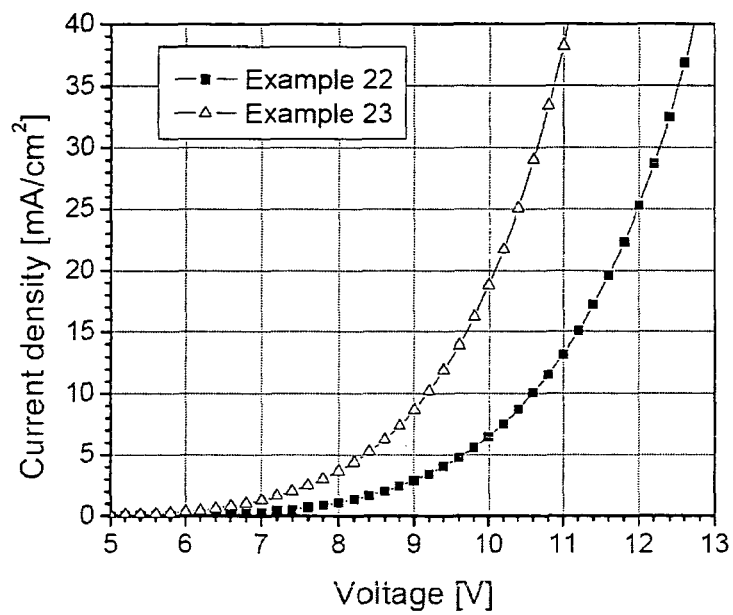
FIG. 29 shows current density vs voltage of H1NT:Ir(pq)$_2$(acac) and H2BT:Ir(3-Meppy)$_3$ devices.
Figure 30:
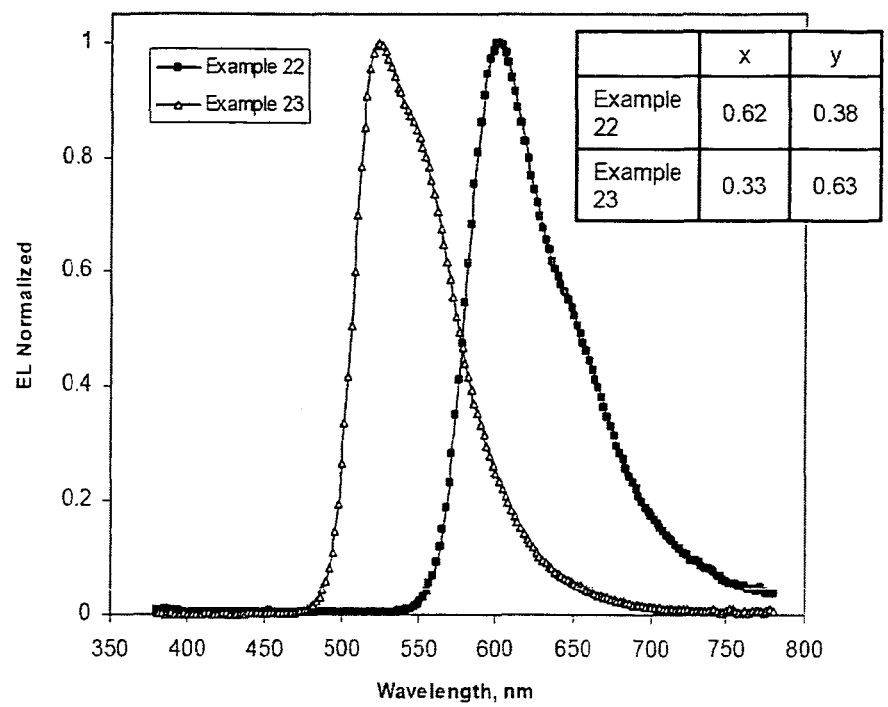
FIG. 30 shows EL and CIE of H1NT:Ir(pq)$_2$(acac) and H2BT:Ir(3-Meppy)$_3$ devices at 10 mA/cm$^2$.
Figure 31:
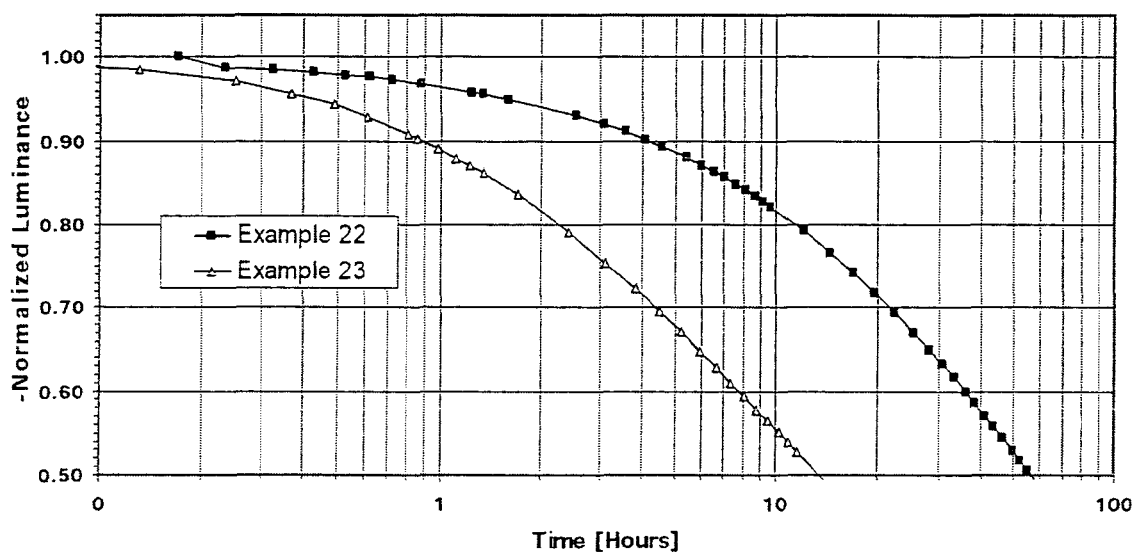
FIG. 31 shows lifetime of H1NT:Ir(pq)$_2$(acac) and H2BT:Ir(3-Meppy)$_3$ devices

The organic stack consists of sequentially, from the ITO surface, 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of the triphenylene compounds or the comparative compounds doped with 6 or 12 wt % of the dopant emitter as the emissive layer (EML). Device Examples 1, 4, 7, 10, 13, 16 and 22 and Comparative Device Examples 1, 2, 3, & 4 consist of 100-150 Å of aluminum(III) bis(2-methyl-8-hydroxyquinolinato)-4-phenylphenolate (BAlq) as the ETL2 and 400-500 Å of tris(8-hydroxyquinolinato)aluminum (Alq$_3$) as the ETL1. Device Examples 2, 5, 8, 11, 14, 19, 20, 21 and 23 and Comparative Device Examples 5 & 6 consist of 50-150 Å of HPT as the ETL2 and 400-500 Å of Alq$_3$ as the ETL1. Device Examples 3, 6, 9, 12, 15 and 18 consist of 400-500 Å of Alq$_3$ as the ETL2 with no ETL1. The exact ETL layer thicknesses are shown in Table 2. Structures for HPT and 2,2-BT and additional examples of triphenylene compounds suitable as host materials are shown in FIG. 17.

The luminous efficiency at 500 cd/m$^2$ for red emitting devices or 1000 cd/m$^2$ for green emitting devices are summarized in Table 2.

The triphenylene compounds show high device efficiency as host materials. Devices with HPT as the host show comparable or higher efficiency than those with the comparative compound CBP as the host.

The current-voltage-luminance (IVL) characteristics and operational stabilities were measured for selected devices and are depicted in FIGS. 3-16 and FIGS. 18-31. The lifetimes of the devices with triphenylene hosts are comparable to those with the comparative compound CBP as the host.

TABLE 2

Summary of device structures and performance of HPT, 2,2-BT, H1NT and H2BT as hosts for various phosphorescent dopants.

| Device Example | Host | EML Dopant (%) | ETL2 (Å) | ETL1 (Å) | Luminous efficiency (cd/A) at (cd/m$^2$) |
|---|---|---|---|---|---|
| Example 1 | HPT | Ir(3-Mepq)$_2$(acac) (12) | BAlq (150) | Alq$_3$ (400) | 13.1 (500) |
| Example 2 | HPT | Ir(3-Mepq)$_2$(acac) (12) | HPT (150) | Alq$_3$ (400) | 13.5 (500) |
| Example 3 | HPT | Ir(3-Mepq)$_2$(acac) (12) | Alq$_3$ (400) | none | 9.5 (500) |
| Comparative Example 1 | CBP | Ir(3-Mepq)$_2$(acac) (12) | BAlq (150) | Alq$_3$ (400) | 13.5 (500) |
| Example 4 | HPT | Ir(1-piq)$_3$ (12) | BAlq (150) | Alq$_3$ (400) | 8.7 (500) |
| Example 5 | HPT | Ir(1-piq)$_3$ (12) | HPT (150) | Alq$_3$ (400) | 8.5 (500) |
| Example 6 | HPT | Ir(1-piq)$_3$ (12) | Alq$_3$ (400) | none | 6.6 (500) |
| Comparative Example 2 | CBP | Ir(1-piq)$_3$ (12) | BAlq (150) | Alq$_3$ (400) | 8.7 (500) |
| Example 7 | HPT | Ir(5'-Phppy)$_3$ (6) | BAlq (100) | Alq$_3$ (400) | 31.6 (1000) |
| Example 8 | HPT | Ir(5'-Phppy)$_3$ (6) | HPT (100) | Alq$_3$ (400) | 43.3 (1000) |

TABLE 2-continued

Summary of device structures and performance of HPT, 2,2-BT, H1NT and H2BT as hosts for various phosphorescent dopants.

| Device Example | Host | EML Dopant (%) | ETL2 (Å) | ETL1 (Å) | Luminous efficiency (cd/A) at (cd/m$^2$) |
|---|---|---|---|---|---|
| Example 9 | HPT | Ir(5'-Phppy)$_3$ (6) | Alq$_3$ (400) | none | 39.4 (1000) |
| Comparative Example 3 | CBP | Ir(5'-Phppy)$_3$ (6) | BAlq (100) | Alq$_3$ (400) | 26.2 (1000) |
| Example 10 | 2,2-BT | Ir(3-Mepq)$_2$(acac) (6) | BAlq (100) | Alq$_3$ (500) | 10.5 (500) |
| Example 11 | 2,2-BT | Ir(3-Mepq)$_2$(acac) (6) | HPT (50) | Alq$_3$ (500) | 10.6 (500) |
| Example 12 | 2,2-BT | Ir(3-Mepq)$_2$(acac) (6) | Alq$_3$ (500) | none | 8.9 (500) |
| Example 13 | 2,2-BT | Ir(1-piq)$_3$ (6) | BAlq (100) | Alq$_3$ (500) | 7.0 (500) |
| Example 14 | 2,2-BT | Ir(1-piq)$_3$ (6) | HPT (50) | Alq$_3$ (500) | 7.0 (500) |
| Example 15 | 2,2-BT | Ir(1-piq)$_3$ (6) | Alq$_3$ (500) | none | 6.3 (500) |
| Example 16 | 2,2-BT | Ir(pq)$_2$(acac) (6) | BAlq (150) | Alq3 (500) | 20.3 (500) |
| Example 17 | 2,2-BT | Ir(pq)$_2$(acac) (6) | HPT (50) | Alq3 (600) | 22.8 (500) |
| Example 18 | 2,2-BT | Ir(pq)$_2$(acac) (6) | none | Alq3 (500) | 17.1 (500) |
| Comparative Example 4 | CBP | Ir(pq)$_2$(acac) (6) | BAlq (150) | Alq3 (500) | 24.6 (500) |
| Comparative Example 5 | CBP | Ir(pq)$_2$(acac) (4.5) | HPT (50) | Alq3 (600) | 32.2 (500) |
| Example 19 | 2,2-BT | Ir(5-Phppy)$_3$ (6) | HPT (50) | Alq3 (450) | 26 (1000) |
| Example 20 | 2,2-BT | Ir(5-Phppy)$_3$ (9) | HPT (50) | Alq3 (450) | 29 (1000) |
| Example 21 | 2,2-BT | Ir(5-Phppy)$_3$ (12) | HPT (50) | Alq3 (450) | 31 (1000) |
| Comparative Example 6 | CBP | Ir(5-Phppy)$_3$ (12) | HPT (50) | Alq3 (450) | 65 (1000) |
| Example 22 | H1NT | Ir(pq)$_2$(acac) (6) | BAlq (150) | Alq3 (450) | 23.6 (500) |
| Example 23 | H2BT | Ir(3-Meppy)$_3$ (10) | HPT (50) | Alq3 (450) | 30.6 (1000) |

Figure 10:
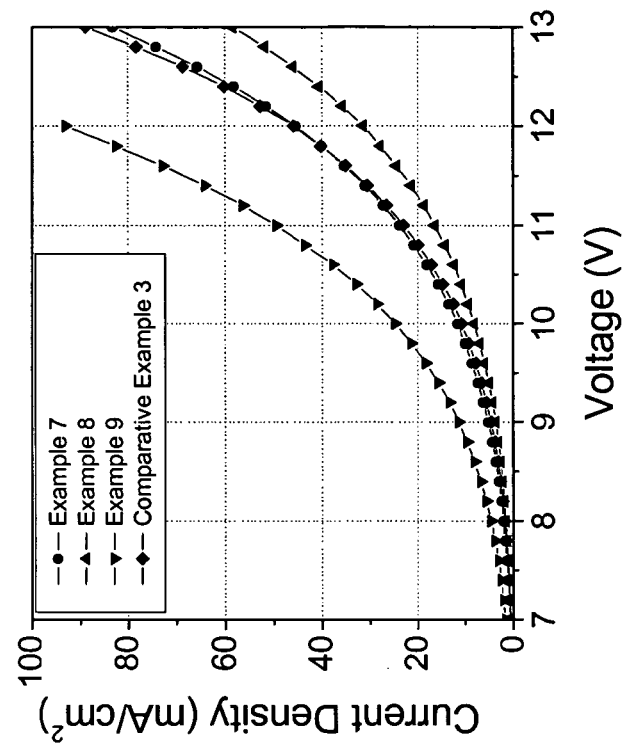
FIG. 10 shows current density vs voltage of Ir(5-Phppy)$_3$ devices.
Figure 9:
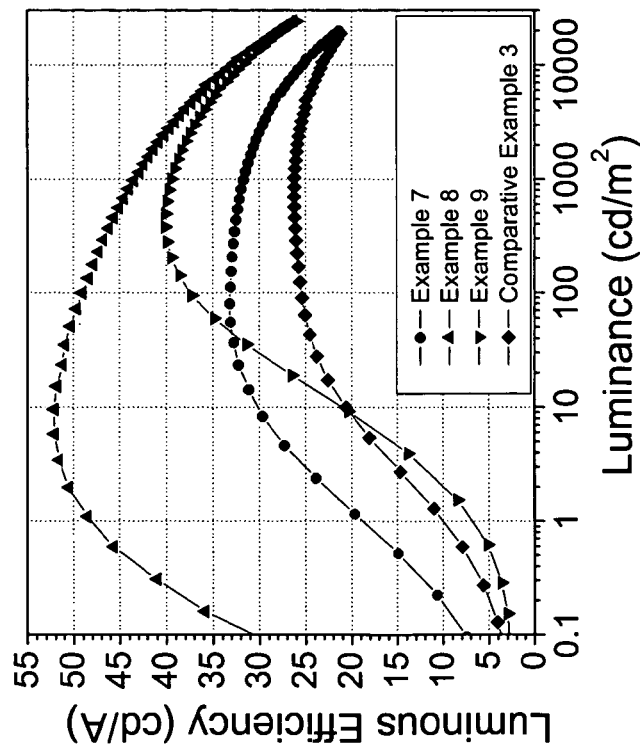
FIG. 9 shows luminous efficiency vs luminance of Ir(5-Phppy)$_3$ devices
Figure 12:
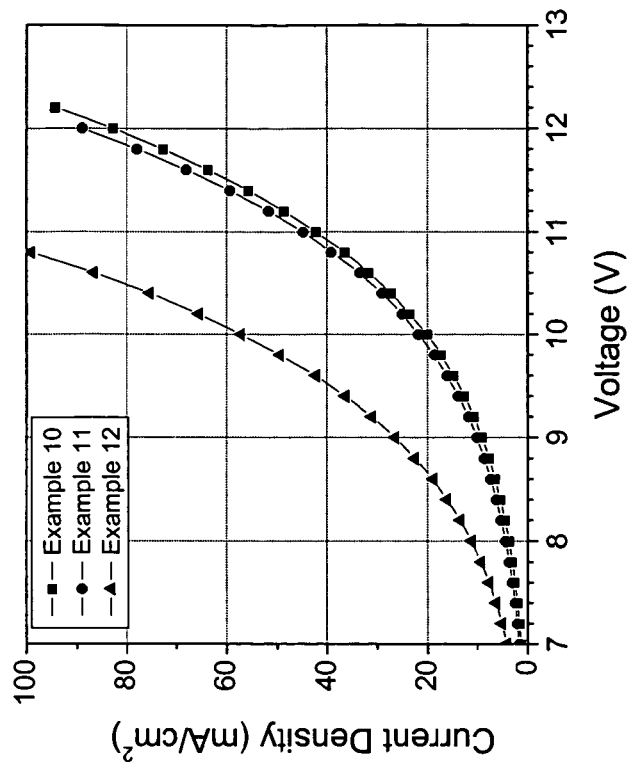
FIG. 12 shows current density vs voltage of 2,2-BT:Ir(3-Mepq)$_2$(acac).
Figure 11:
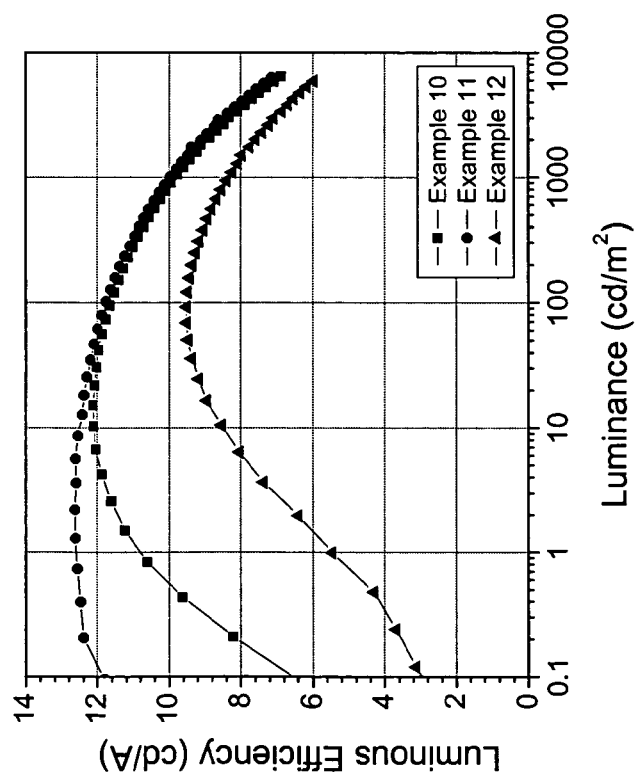
FIG. 11 shows luminous efficiency vs luminance of 2,2-bistriphenylene (2,2-BT) Ir(3-Mepq)$_2$(acac) devices.
Figure 13:
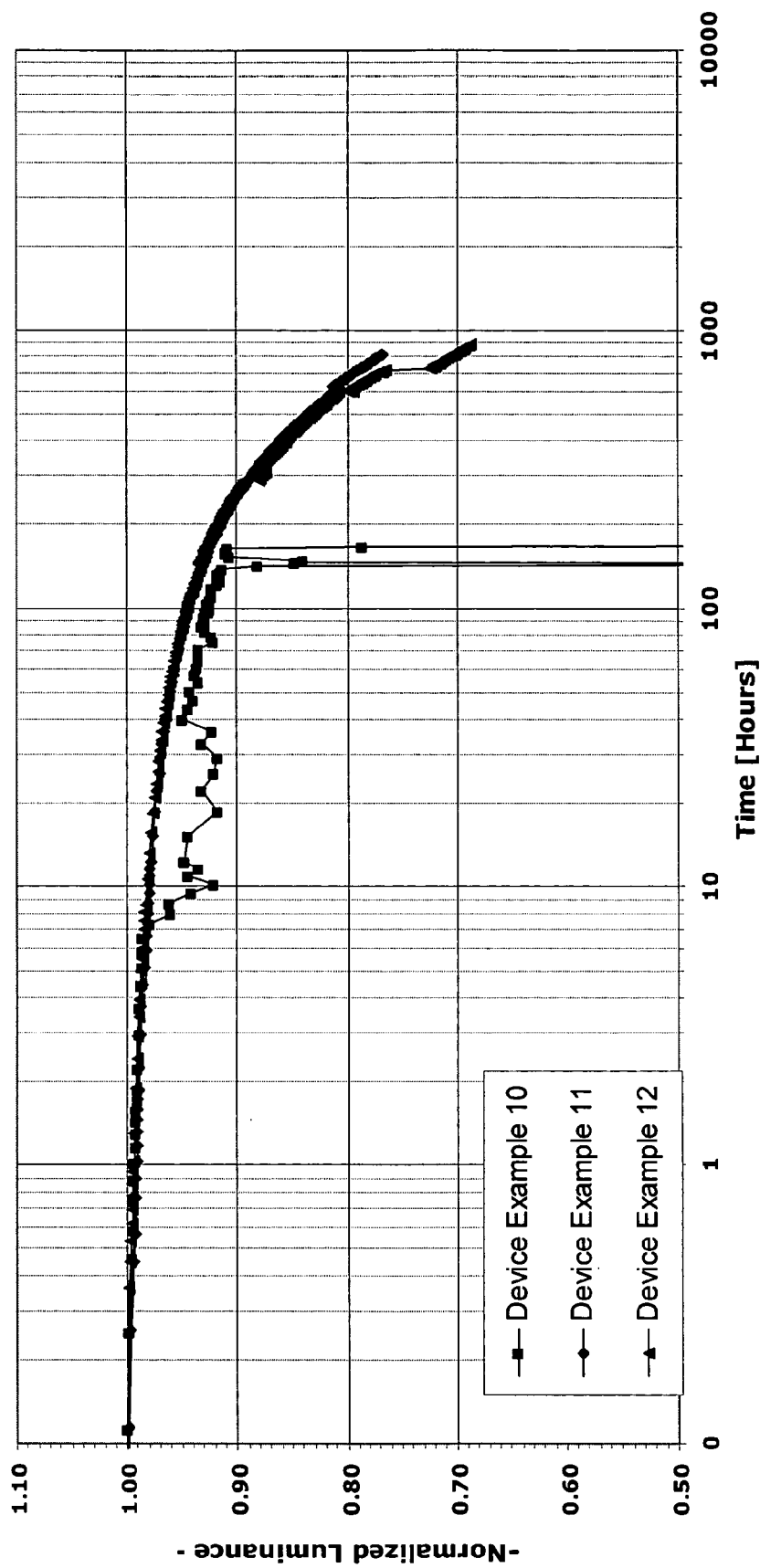
FIG. 13 shows lifetime of 2,2-BT:Ir(3-Mepq)$_2$(acac) devices.
Figure 15:
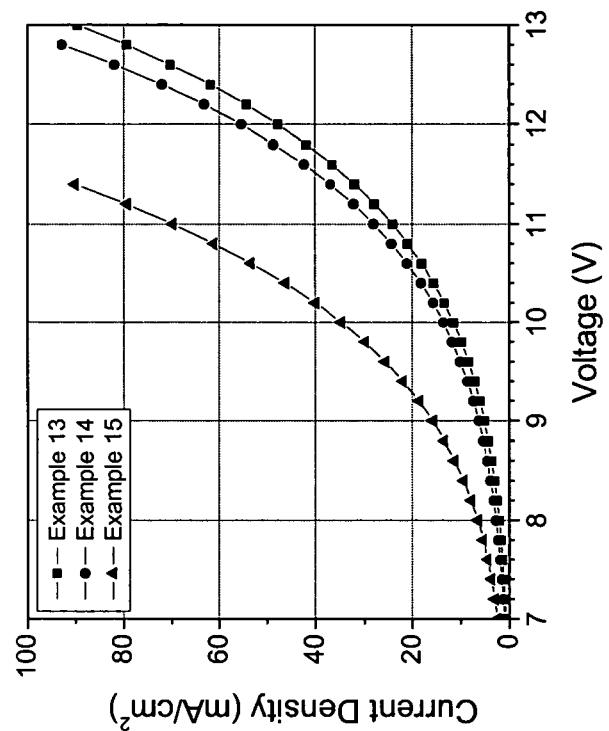
FIG. 15 shows current density vs voltage of 2,2-BT:Ir(1-piq)$_3$ devices.
Figure 14:
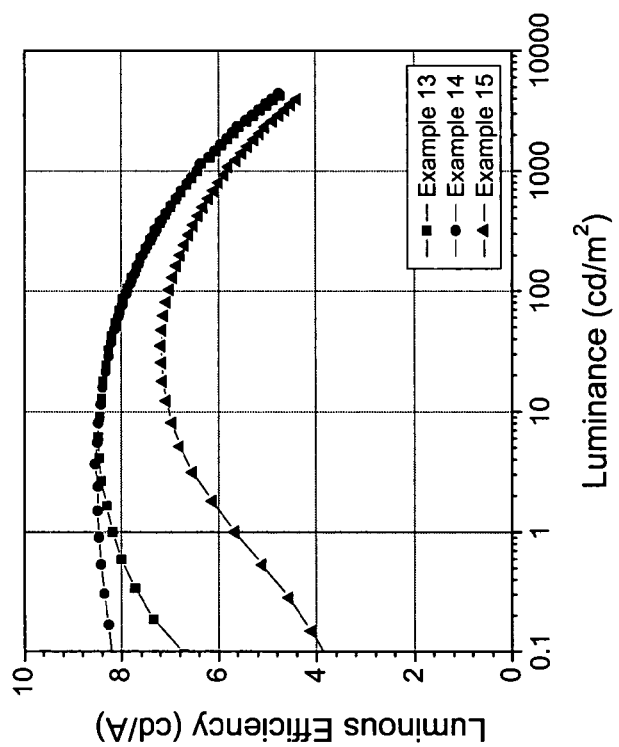
FIG. 14 shows luminous efficiency vs luminance of 2,2-BT:Ir(1-piq)$_3$ devices
Figure 16:
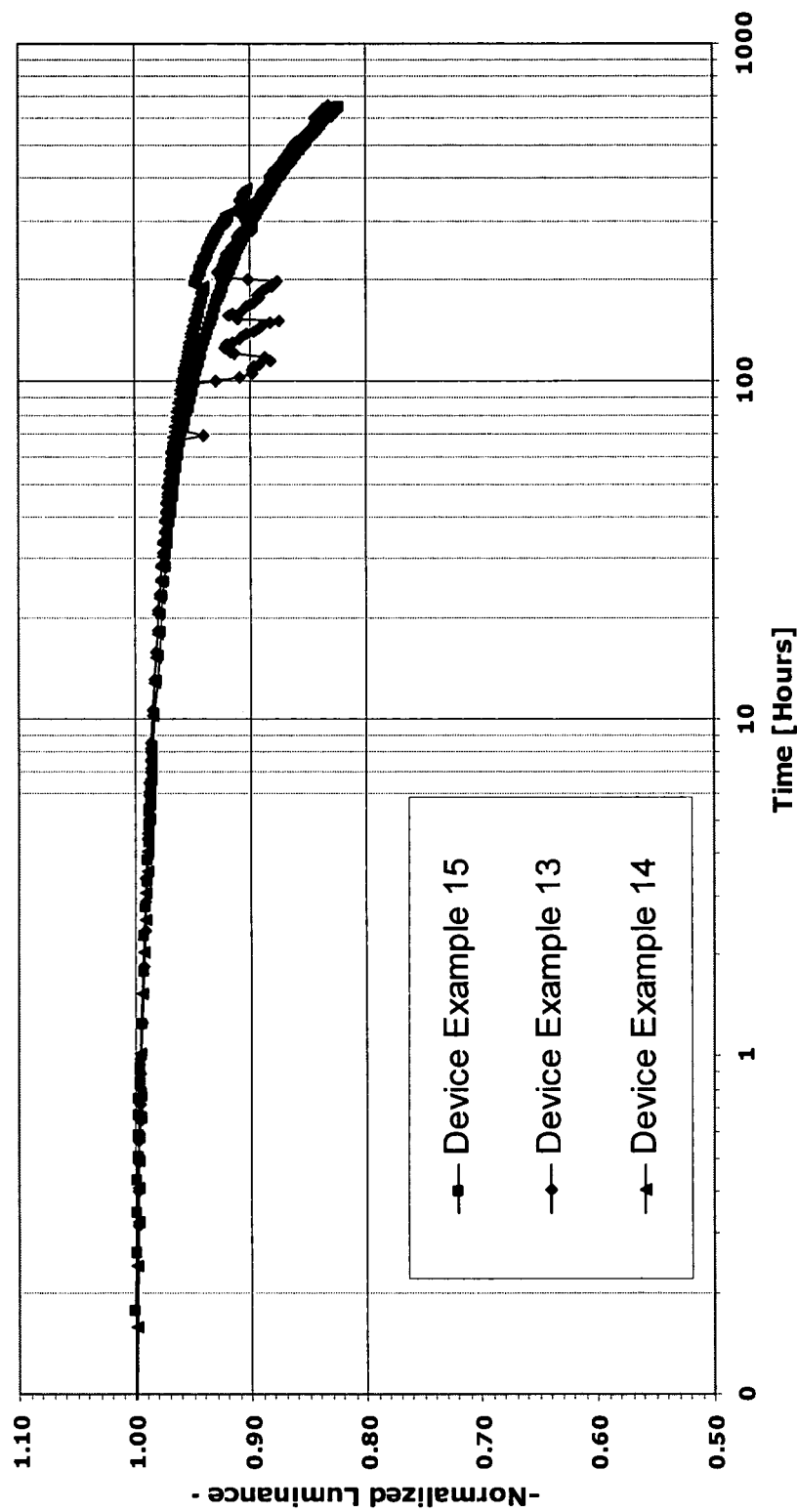
FIG. 16 shows lifetime of 2,2-BT:Ir(1-piq)$_3$ devices.

Phosphorescent devices with very high device efficiency are highly desirable in applications such as display, lighting, etc. For full color and lighting application, high operational stability in red, green and blue colors is essential. Due to the high triplet energy nature of blue phosphorescent dopant emitters, high triplet energy host materials are required so that high device efficiency can be obtained. In OLEDs, polyaromatic compounds with extended π-conjugation usually show respectable lifetimes. However, polyaromatic compounds with extended n-conjugation usually have low triplet energy also. For example, anthracene has a triplet energy of 1.8 eV which is lower than those of red phosphorescent dopants such as Ir(1-piq)$_2$(acac). As a result, a device with an anthracene compound as the host with Ir(1-piq)$_2$(acac) as the dopant emitter is very inefficient, because of quenching. Reducing one fused phenyl ring from anthracene gives naphthalene which is the smallest fused polyaromatic compound. Yet it still has a triplet energy of 2.6 eV which is lower than those of deep blue phosphorescent dopants such as Ir(4,6-F$_2$-5CN-ppy)$_3$. However, triphenylene, despite its four fused ring configuration, has a triplet energy of 2.9 eV which is believed to be suitable for deep blue phosphorescent dopants such as Ir(4,6-F$_2$-5CNppy)$_3$. Triphenylene can be derivatized in various ways such as adding alkyl or aryl groups, linking multiple or fusing triphenylenes through different positions to modulate the electronic properties (e.g. conjugation, triplet energy, HOMO/LUMO levels, etc), structure properties (e.g., planar, non-planar, chirality), and physical properties (e.g., sublimation temperature, solubility). The unique property that triphenylene compounds provides relatively large degree of π-conjugation but relatively high triplet energy renders them very suitable for stable and high-efficiency PHOLEDs. For example, hexaphenyltriphenylene (HPT) as a host for red dopant Ir(3-Mepq)$_2$(acac) and Ir(1-piq)$_3$ gives efficient and highly stable devices as shown in FIGS. 3-5 and 6-8 respectively. While devices with 2,2-bistriphenylene (2,2-BT) as the host show lower efficiency than those with the comparative compound CBP as the host, utilizing 2,2-BT as a host for red dopants Ir(3-Mepq)$_2$(acac) and Ir(1-piq)$_3$ resulted in relatively efficient and highly stable devices as shown in FIGS. 9-11 (11-13) and 12-14 (14-16) respectively.

We claim:

1. An emissive layer comprising a phosphorescent material and a triphenylene compound having the formula:

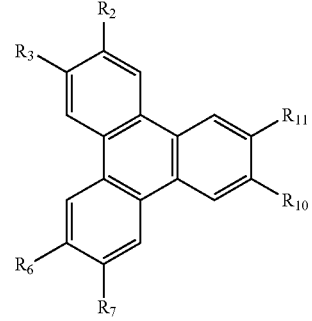

wherein $R_2$, $R_3$, $R_6$, $R_7$, $R_{10}$, and $R_{11}$ is each independently a pendant substituent selected from the group consisting of aryl, substituted aryl, heteroaryl, substituted heteroaryl, alkyl, arylkyl, heteroalkyl, alkenyl, and alkynyl; and wherein the triphenylene compound has a molecular weight of less than 1400.

2. The emissive layer of claim 1 wherein at least one of $R_2$, $R_3$, $R_6$, $R_7$, $R_{10}$, or $R_{11}$ is selected from aryl and substituted aryl.

3. The emissive layer of claim 1 wherein $R_2$, $R_3$, $R_6$, $R_7$, $R_{10}$, and $R_{11}$ are all the same.

4. The emissive layer of claim 1 wherein $R_2$, $R_3$, $R_6$, $R_7$, $R_{10}$, and $R_{11}$ are selected from a phenyl group, naphthyl group, and biphenyl group.

5. The emissive layer of claim 3 wherein $R_2$, $R_3$, $R_6$, $R_7$, $R_{10}$, and $R_{11}$ are selected from a phenyl group, naphthyl group, and biphenyl group.

6. The emissive layer of claim 1, wherein $R_2$, $R_3$, $R_6$, $R_7$, $R_{10}$, and $R_{11}$ is each selected from the group consisting of aryl, substituted aryl, heteroaryl, and substituted heteroaryl.

7. The emissive layer of claim 6, wherein $R_2$, $R_3$, $R_6$, $R_7$, $R_{10}$, and $R_{11}$ is each aryl or substituted aryl.

8. The emissive layer of claim 1, wherein $R_2$, $R_3$, $R_6$, $R_7$, $R_{10}$, and $R_{11}$ are all identically a phenyl group, naphthyl group, or biphenyl group.

9. The emissive layer of claim 1 wherein the triphenylene compound is selected from the group consisting of
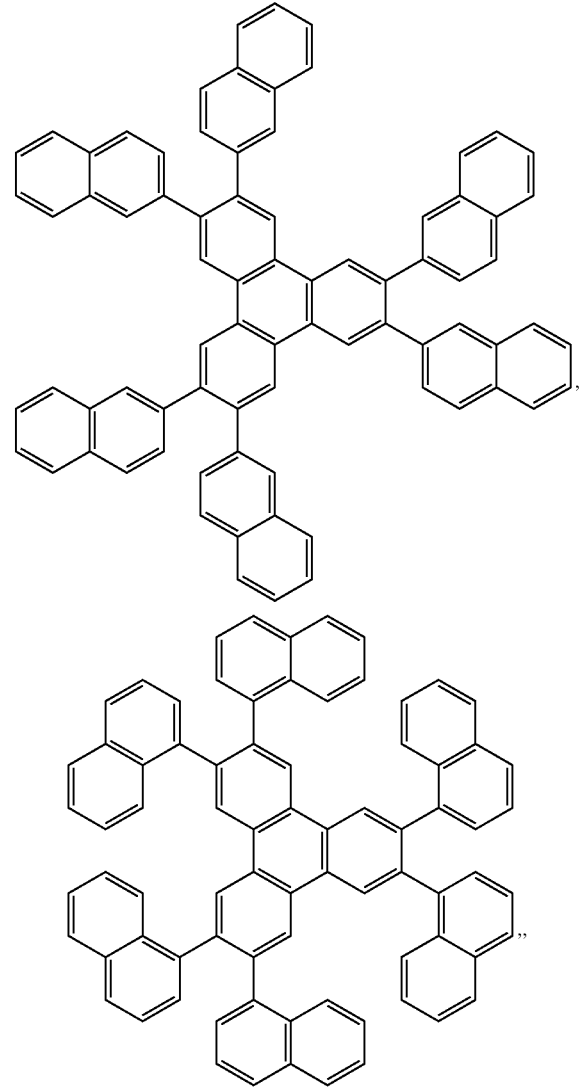
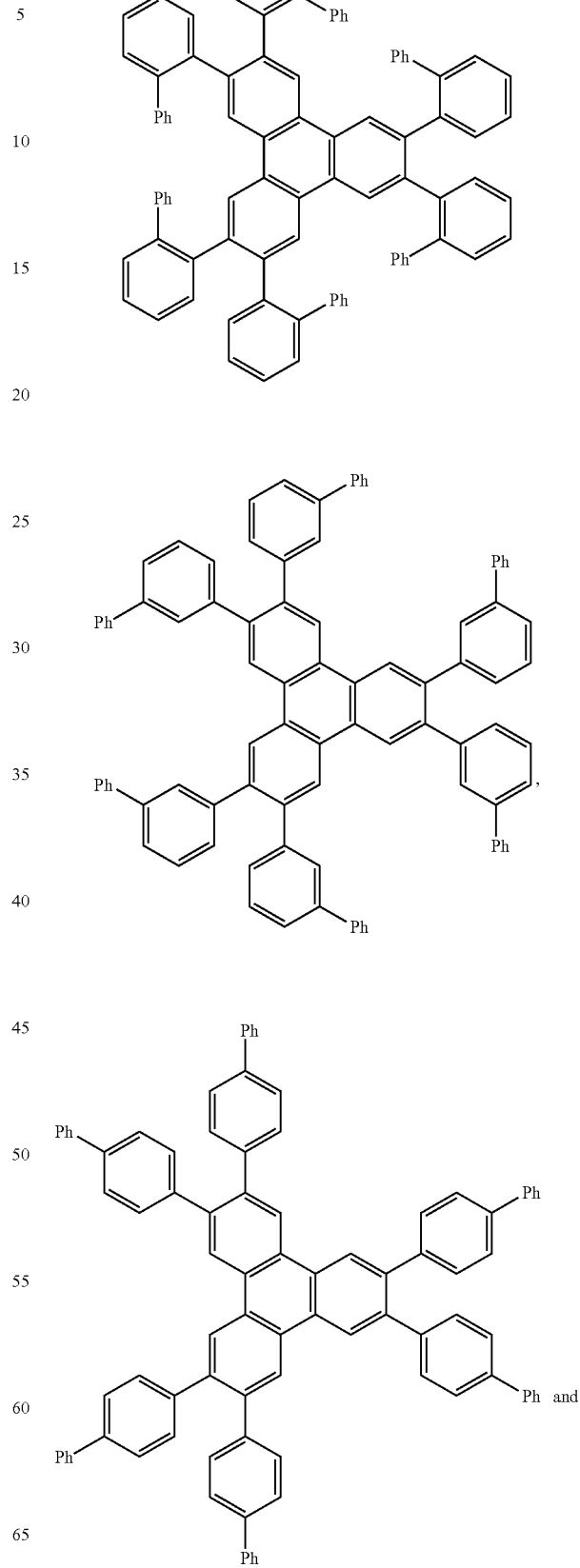

-continued

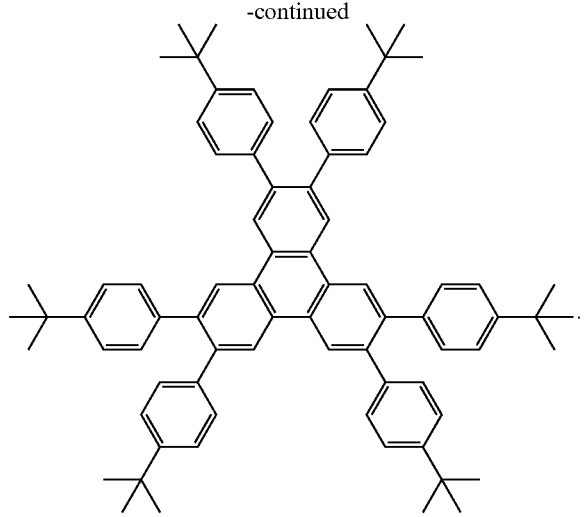

10. The emissive layer of claim 1, wherein the triphenylene compound is:

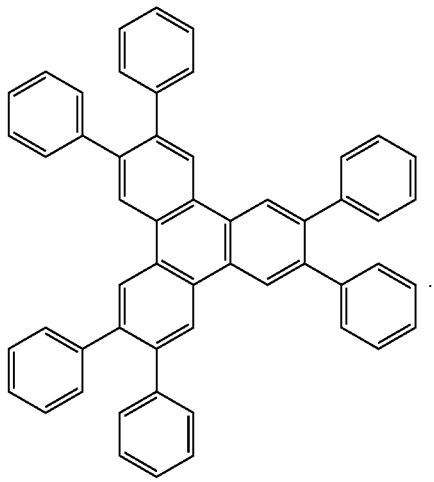 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1]

11. The emissive layer of claim 1 wherein the triphenylene compound has an energy gap between its HOMO and the LUMO energy levels that is larger than the energy gap between the HOMO and the LUMO energy levels of the phosphorescent material.

12. The emissive layer of claim 1 wherein the triphenylene compound has an energy gap between its HOMO energy level and its LUMO energy level of at least about 1.8 eV.

13. The emissive layer of claim 1 wherein the triphenylene compound has a highest occupied molecular orbital that is lower than the highest occupied molecular orbital of the phosphorescent material.

14. The emissive layer of claim 1 wherein the triphenylene compound has a lowest unoccupied molecular orbital that is higher than the lowest unoccupied molecular orbital of the phosphorescent material.

15. The emissive layer of claim 1, wherein phosphorescent material is a blue-emitting phosphorescent material.

16. An organic electroluminescent device comprising:
an anode;
a cathode;
an emissive layer of claim 1 between the anode and the cathode.

17. The device of claim 16, wherein phosphorescent material is a blue-emitting phosphorescent material.

18. The device of claim 16, wherein the triphenylene compound is:

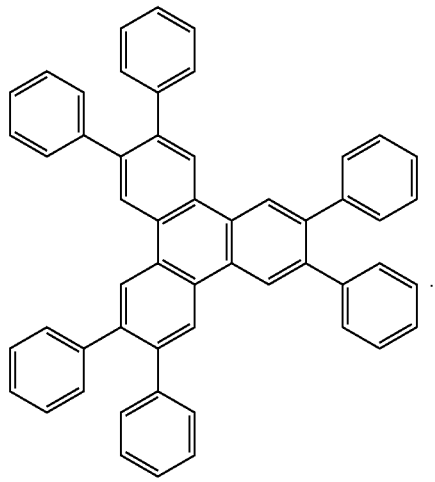 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1]

19. The device of claim 16, wherein the triphenylene compound is selected from the group consisting of

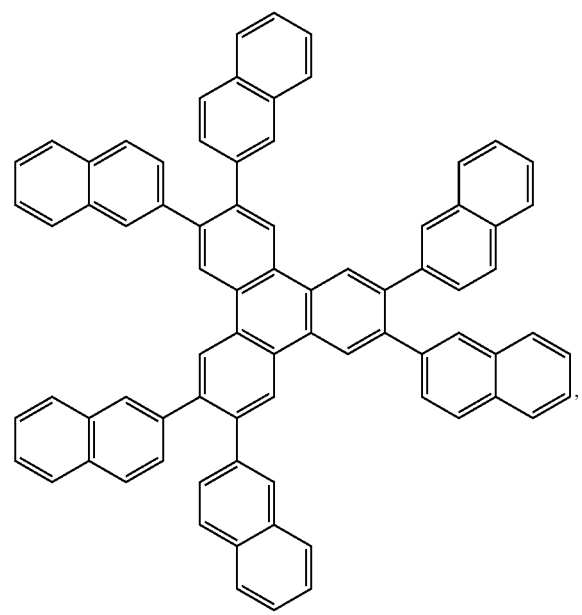

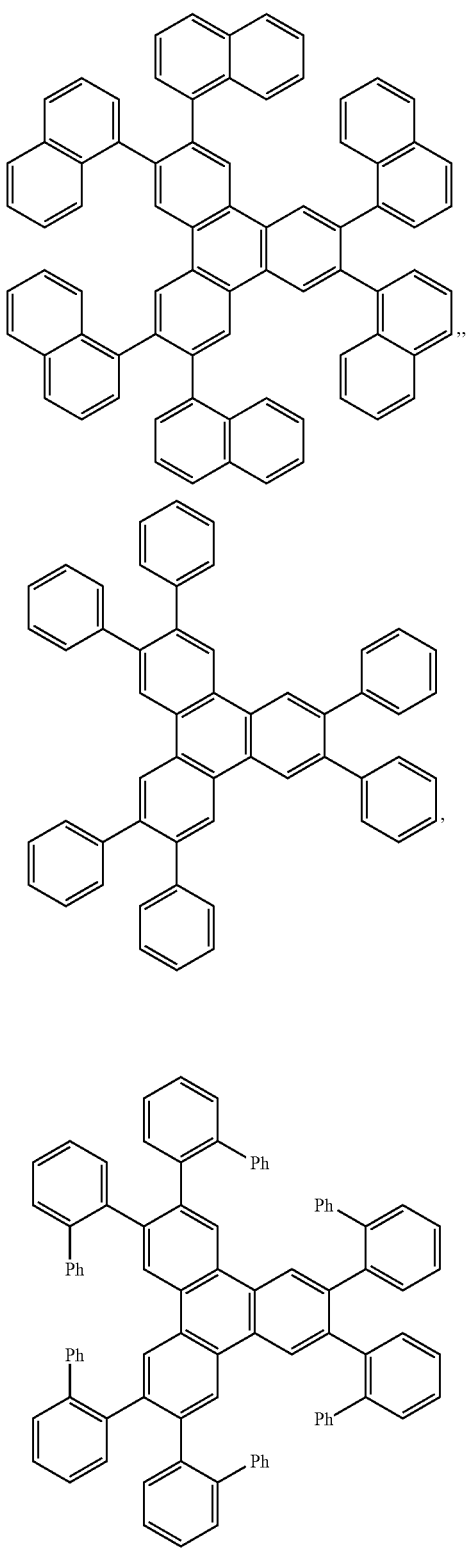
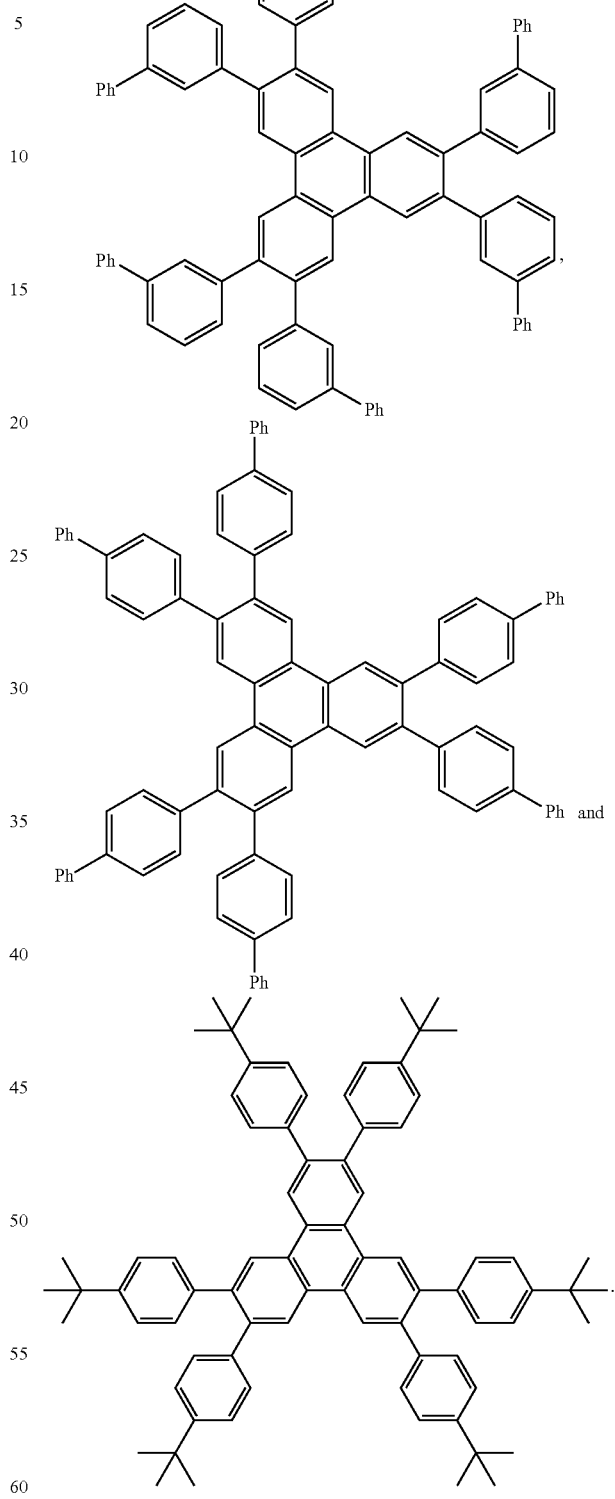
* * * * *